(12) United States Patent
Murase et al.

(10) Patent No.: US 8,084,146 B2
(45) Date of Patent: Dec. 27, 2011

(54) LIGHT-EMITTING DEVICE MATERIAL AND LIGHT-EMITTING DEVICE

(75) Inventors: Seiichiro Murase, Otsu (JP); Daisuke Kitazawa, Otsu (JP); Kazumasa Nagao, Otsu (JP); Kazunori Sugimoto, Otsu (JP); Tsuyoshi Tominaga, Otsu (JP)

(73) Assignee: Toray Industries, Inc., Tokyo (JP)

( * ) Notice: Subject to any disclaimer, the term of this patent is extended or adjusted under 35 U.S.C. 154(b) by 933 days.

(21) Appl. No.: 11/597,591

(22) PCT Filed: May 19, 2005

(86) PCT No.: PCT/JP2005/009118
§ 371 (c)(1),
(2), (4) Date: Nov. 21, 2006

(87) PCT Pub. No.: WO2005/113531
PCT Pub. Date: Dec. 1, 2005

(65) Prior Publication Data
US 2007/0247063 A1    Oct. 25, 2007

(30) Foreign Application Priority Data

May 21, 2004  (JP) ................ 2004-151463
May 31, 2004  (JP) ................ 2004-160734

(51) Int. Cl.
*H01L 51/54* (2006.01)
*C09K 11/00* (2006.01)

(52) U.S. Cl. .......... 428/690; 428/917; 549/43; 549/460; 313/504; 313/506; 252/301.16; 257/40

(58) Field of Classification Search ............... 428/690, 428/917; 313/504, 506; 257/E51.04; 514/385, 514/396, 399; 252/519.2, 301; 532/1; 523/209, 523/212
See application file for complete search history.

(56) References Cited

U.S. PATENT DOCUMENTS
| | | | |
|---|---|---|---|
| 6,720,090 B2 | 4/2004 | Young et al. | |
| 2004/0076853 A1* | 4/2004 | Jarikov | .............. 428/690 |
| 2004/0161633 A1 | 8/2004 | Seo et al. | |

FOREIGN PATENT DOCUMENTS
| | | |
|---|---|---|
| EP | 1695952 A | 8/2006 |
| JP | 03-205479 | 9/1991 |
| JP | 09-268283 | 10/1997 |
| JP | 11-241062 | 9/1999 |
| JP | 11-297473 | 10/1999 |
| JP | 2000-273056 | 10/2000 |
| JP | 2002-260861 | 9/2002 |
| JP | 2003-31371 | 1/2003 |
| JP | 2003-128651 | 5/2003 |
| JP | 2003-146951 | 5/2003 |
| JP | 2003146951 | * 5/2003 |
| JP | 2003-306454 | 10/2003 |
| JP | 2004-002351 | 1/2004 |
| JP | 2004-210786 | 7/2004 |
| JP | 2005-47868 | 2/2005 |
| JP | 2005-108692 | 4/2005 |
| WO | 2004/020388 A | 3/2004 |
| WO | 2006/104221 A | 10/2006 |

OTHER PUBLICATIONS
Tang and VanSlyke. (1987). "Organic electroluminecent diodes," *Applied Physics Letters* 51(12): 913-915.
Supplementary European Search Report in related application EP 05 74 1416 mailed Apr. 21, 2010.

* cited by examiner

*Primary Examiner* — Jennifer Chriss
*Assistant Examiner* — Michael H Wilson
(74) *Attorney, Agent, or Firm* — Pillsbury Winthrop Shaw Pittman LLP

(57) ABSTRACT

The present invention is a light emitting device material characterized by containing an anthracene compound represented by the following general formula (1), and the present invention allows a light emitting device having high luminous efficiency and excellent durability.

[Chemical formula 1]

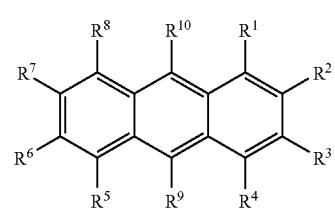

(1)

($R^1$ to $R^{10}$ are a hydrogen atom, alkyl group, cycloalkyl group, heterocyclic group or the like. At least one of the $R^1$ to $R^{10}$ is a substituent represented by the following general formula (2))

[Chemical formula 2]

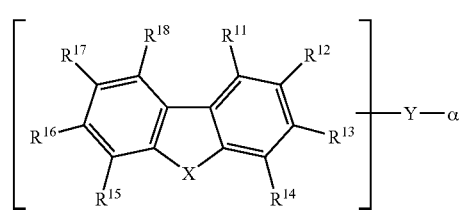

(2)

5 Claims, No Drawings

LIGHT-EMITTING DEVICE MATERIAL AND LIGHT-EMITTING DEVICE

REFERENCE TO RELATED APPLICATION

This application is a national stage of PCT/JP2005/009118, which was published on Dec. 1, 2005, and which claims the benefit of priority to Japanese Application Nos. 2004-151463, filed May 21, 2004 and 2004-160734, filed May 31, 2004.

TECHNICAL FIELD

The present invention relates to a light emitting device material useful as a fluorescent dye and a charge transporting material, and to a light emitting device using this material, which can be utilized in the fields such as display device, flat-panel display, backlight, illumination, interior, mark, signboard, electrophotographic apparatus and light signal generator.

BACKGROUND ART

In recent years, the studies of an organic thin-film light emitting device (LED: light emitting device) have actively been conducted such that an electron injected from a cathode and a hole injected from an anode emit light when recombining in an organic fluorescent compound held between both of the cathode and the anode. This emitting device is characterized by thin type, high brightness under low driving voltages and multicolor light emission through selection of light-emitting materials, thereby attracting notice.

These studies have been conducted by many research institutions since it was revealed by C. W. Tang et al. of Eastman Kodak Company that an organic thin-film device emitted light with high brightness. The typical structure of an organic thin-film emitting device presented by a study group of the Kodak Company is such that a diamine compound for hole transporting, tris(8-quinolinolate)aluminum (III) as a luminescent layer and Mg:Ag (alloy) as a cathode are sequentially layered on an ITO glass substrate, which emitting device allows green light emission of 1000 cd/m² at a driving voltage of approximately 10 V (refer to Nonpatent Document 1).

The use of various fluorescent materials for a luminescent layer allows an organic thin-film emitting device to obtain diverse luminescent colors, so that the studies of practical application to displays are active. Among light-emitting materials of the three primary colors, the studies of green light-emitting materials are the most advanced, and the earnest studies in red light-emitting materials and blue light-emitting materials are presently made toward performance improvement.

One of the largest problems in an organic thin-film light emitting device is to improve durability of the device. In particular, with regard to a blue light emitting device, few blue light-emitting materials provide a device having excellent durability and high reliability. For example, a technique is disclosed in which an anthracene compound is used for a blue light emitting device light emitting device. Blue light emitting devices using various anthracene compounds (refer to Patent Documents 1 to 6) are reported; however, any of them has insufficient durability.

Non-patent Document 1: Applied Physics Letters (USA) 1987, Vol. 51, No. 12, pp 913 to 915
Patent Document 1: Japanese Unexamined Patent Publication No. 11-297473 (Claims)
Patent Document 2: Japanese Unexamined Patent Publication No. 2000-273056 (Claims)
Patent Document 3: Japanese Unexamined Patent Publication No. 2002-260861 (claim 4)
Patent Document 4: Japanese Unexamined Patent Publication No. 2003-128651 (Claims)
Patent Document 5: Japanese Unexamined Patent Publication No. 2003-306454 (claim 1, paragraph 0039)
Patent Document 6: Japanese Unexamined Patent Publication No. 2004-2351 (claim 1, paragraphs 0049 to 0050)

DISCLOSURE OF THE INVENTION

Problems to be Solved by the Invention

As described above, a blue light emitting device having high luminous efficiency and excellent durability has not been provided in conventional organic thin-film light emitting devices. Then, the present invention is intended to solve problems in the prior art and to provide a light emitting device material allowing a blue light emitting device having high luminous efficiency and excellent durability, and a light emitting device using this material.

Means for Solving the Problem

The present invention is a light emitting device material comprising an anthracene compound represented by the following general formula (1) or general formula (3).

[Chemical formula 1]

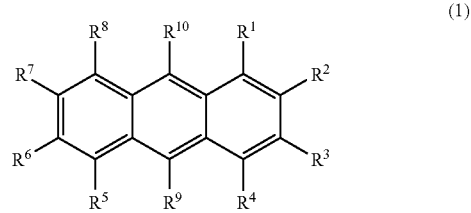

(1)

(Wherein, $R^1$ to $R^{10}$ each may be the same or different and are selected from among a hydrogen atom, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, cyano group, carbonyl group, carboxyl group, oxycarbonyl group, carbamoyl group, amino group, silyl group and phosphine oxide group. At least one of the $R^1$ to $R^{10}$ is a substituent represented by the following general formula (2)

[Chemical formula 2]

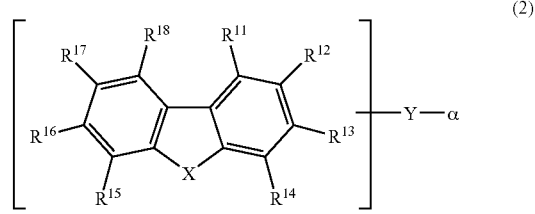

(2)

(Wherein, $R^{11}$ to $R^{18}$ each may be the same or different and are selected from among a hydrogen atom, alkyl group, cycloalkyl group, alkoxy group, phenyl group, naphtyl group and heteroaryl group. X represents an oxygen atom or sulfur atom, and Y is selected from among a single bond, arylene group and heteroarylene group. Any one of the $R^{11}$ to $R^{18}$ is used for linking with Y, and α is used for linking with the anthracene skeleton.).)

[Chemical formula 3]

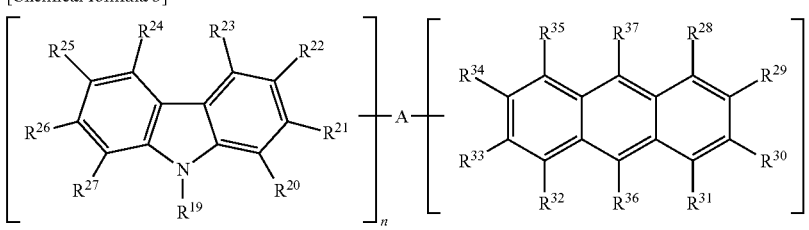

(Wherein, $R^{19}$ to $R^{37}$ each may be the same or different and are selected from among a hydrogen atom, alkyl group, cycloalkyl group, heterocyclic group, alkoxy group, alkylthio group, arylether group, arylthioether group, phenyl group, alkyl substituted phenyl group, alkoxy substituted phenyl group, aryl substituted phenyl group, naphtyl group, alkyl substituted naphtyl group, alkoxy substituted naphtyl group, aryl substituted naphtyl group, phenanthryl group, alkyl substituted phenanthryl group, alkoxy substituted phenanthryl group, aryl substituted phenanthryl group, heteroaryl group and silyl group. n is 1 or 2. A is a heteroarylene group or arylene group with a carbon number of 6 or more to 12 or less. Any one of the $R^{19}$ to $R^{27}$ and any one of the $R^{28}$ to $R^{37}$ are used for linking with A.)

The present invention is a light emitting device wherein at least a luminescent layer exists between an anode and a cathode to emit light by electric energy, and by containing a light emitting device material represented by the general formula (1) or the general formula (3).

Advantageous Effect of the Invention

The present invention can provide a light emitting device material utilizable for a light emitting device and excellent in thin film stability. In addition, the present invention allows a light emitting device having high luminous efficiency and excellent durability.

DETAILED DESCRIPTION OF THE PREFERRED EMBODIMENTS

An anthracene compound represented by the general formula (1) or the general formula (3) in the present invention is explained in detail

[Chemical formula 4]

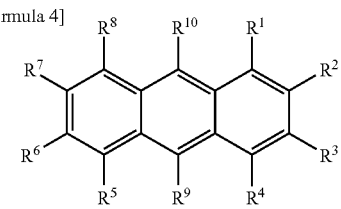

(1)

$R^1$ to $R^{10}$ each may be the same or different and are selected from among a hydrogen atom, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, cyano group, carbonyl group, carboxyl group, oxycarbonyl group, carbamoyl group, amino group, silyl group and phosphine oxide group. At least one of the $R^1$ to $R^{10}$ is a substituent represented by the following general formula (2)

[Chemical formula 5]

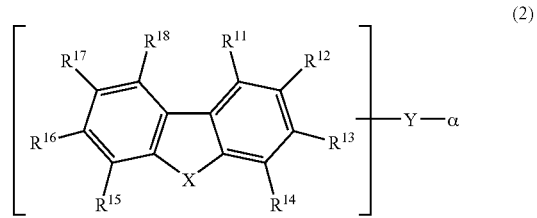

(2)

($R^{11}$ to $R^{18}$ each may be the same or different and are selected from among a hydrogen atom, alkyl group, cycloalkyl group, alkoxy group, phenyl group, naphtyl group and heteroaryl group. X represents an oxygen atom or sulfur atom, and Y is selected from among a single bond, arylene group and heteroarylene group. Any one of the $R^{11}$ to $R^{18}$ is used for linking with Y, and α is used for linking with the anthracene skeleton.).

[Chemical formula 6]

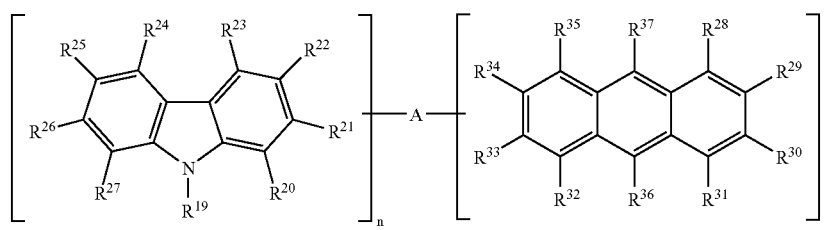

(3)

$R^{19}$ to $R^{37}$ each may be the same or different and are selected from among a hydrogen atom, alkyl group, cycloalkyl group, heterocyclic group, alkoxy group, alkylthio group, arylether group, arylthioether group, phenyl group, alkyl substituted phenyl group, alkoxy substituted phenyl group, aryl substituted phenyl group, naphtyl group, alkyl substituted naphtyl group, alkoxy substituted naphtyl group, aryl substituted naphtyl group, phenanthryl group, alkyl substituted phenanthryl group, alkoxy substituted phenanthryl group, aryl substituted phenanthryl group, heteroaryl group and silyl group. n is 1 or 2. A is a heteroarylene group or arylene group with a carbon number of 6 or more to 12 or less. Any one of the $R^{19}$ to $R^{27}$ and any one of the $R^{28}$ to $R^{37}$ are used for linking with A.

Among these substituents, an alkyl group denotes saturated aliphatic hydrocarbon groups such as a methyl group, ethyl group, n-propyl group, isopropyl group, n-butyl group, sec-butyl group and tert-butyl group, which alkyl group may have a substituent or not. An added substituent in the case of being substituted is not particularly limited, for example, including an alkyl group, aryl group and heteroaryl group; this point is common to the following description also. The carbon number of an alkyl group is not particularly limited, being in a range of typically 1 or more to 20 or less, preferably 1 or more to 8 or less in view of availability and costs.

A cycloalkyl group denotes saturated alicyclic hydrocarbon groups such as cyclopropyl, cyclohexyl, norbornyl and adamanthyl, which cycloalkyl group may have a substituent or not. The carbon number of an alkyl group portion is not particularly limited, being in a range of typically 3 or more to 20 or less.

A heterocyclic group denotes alicyclic rings having an atom except carbon in a ring, such as a pyran ring, piperidine ring and cyclic amide, which heterocyclic group may have a substituent or not. The carbon number of a heterocyclic group is not particularly limited, being in a range of typically 2 or more to 20 or less.

An alkenyl group denotes unsaturated aliphatic hydrocarbon groups containing a double bond, such as a vinyl group, allyl group and butadienyl group, which alkenyl group may have a substituent or not. The carbon number of an alkenyl group is not particularly limited, being in a range of typically 2 to 20.

A cycloalkenyl group denotes unsaturated alicyclic hydrocarbon groups containing a double bond, such as a cyclopentenyl group, cyclopentadienyl group and cyclohexenyl group, which cycloalkenyl group may have a substituent or not.

An alkynyl group denotes an unsaturated aliphatic hydrocarbon group containing a triple bond, such as an ethinyl group, which alkynyl group may have a substituent or not. The carbon number of an alkynyl group is not particularly limited, being in a range of typically 2 to 20.

An alkoxy group denotes functional groups in which aliphatic hydrocarbon groups are bonded through an ether bond, such as a methoxy group, ethoxy group and propoxy group, which aliphatic hydrocarbon groups may have a substituent or not. The carbon number of an alkoxy group is not particularly limited, being in a range of typically 1 or more to 20 or less.

An alkylthio group is such that an oxygen atom of an ether bond of an alkoxy group is substituted with a sulfur atom. A hydrocarbon group of an alkylthio group may have a substituent or not. The carbon number of an alkylthio group is not particularly limited, being in a range of typically 1 or more to 20 or less.

An arylether group denotes a functional group in which aromatic hydrocarbon groups are bonded through an ether bond, such as a phenoxy group, which aromatic hydrocarbon groups may have a substituent or not. The carbon number of an arylether group is not particularly limited, being in a range of typically 6 or more to 40 or less.

An arylthioether group is such that an oxygen atom of an ether bond of an arylether group is substituted with a sulfur atom. Aromatic hydrocarbon groups in an arylthioether group may have a substituent or not. The carbon number of an arylether group is not particularly limited, being in a range of typically 6 or more to 40 or less.

An aryl group denotes aromatic hydrocarbon groups such as a phenyl group, naphtyl group, biphenyl group, phenanthryl group, terphenyl group and pyrenyl group. An aryl group may have a substituent or not. The carbon number of an aryl group is not particularly limited, being in a range of typically 6 to 40.

A heteroaryl group denotes aromatic groups having an atom except carbon in a ring, such as a furanyl group, thiophenyl group, oxazolyl group, pyridyl group, quinolinyl group and carbazolyl group, which heteroaryl group may have a substituent or not. The carbon number of a heteroaryl group is not particularly limited, being in a range of typically 2 to 30.

A halogen atom denotes fluorine, chlorine, bromine and iodine.

A carbonyl group, carboxyl group, oxycarbonyl group, carbamoyl group, amino group and phosphine oxide group may have a substituent or not, for example, which includes an alkyl group, cycloalkyl group, aryl group and heteroaryl group, and these substituents may further be substituted.

A silyl group denotes a functional group having a bond to a silicon atom, such as a trimethylsilyl group, which silyl group may have a substituent or not. The carbon number of a silyl group is not particularly limited, being in a range of typically 3 to 20. The number of silicon atoms is typically 1 to 6.

An arylene group denotes a divalent group derived from aromatic hydrocarbon groups such as a phenyl group, naphtyl group, biphenyl group, phenanthryl group, terphenyl group and pyrenyl group, which arylene group may have a substituent or not. The carbon number of an arylene group is not particularly limited, being in a range of typically 6 to 40. In the case where A of the general formula (3) is an arylene group, the arylene group may have a substituent or not and the carbon number thereof is in a range of 6 to 12 including a substituent.

A heteroarylene group denotes a divalent group derived from aromatic groups having an atom except carbon, such as a furanyl group, thiophenyl group, oxazolyl group, pyridyl group, quinolinyl group and carbazolyl group, which heteroarylene group may have a substituent or not. The carbon number of a heteroarylene group is not particularly limited, being in a range of typically 2 to 30.

An alkyl substituted phenyl group denotes a phenyl group substituted with the above-mentioned alkyl group, and the number of alkyl groups is in a range of 1 or more to 5 or less and the kind of them may be the same or different.

An alkoxy substituted phenyl group denotes a phenyl group substituted with the above-mentioned alkoxy group, and the number of alkoxy groups is in a range of 1 or more to 5 or less and the kind of them may be the same or different.

An aryl substituted phenyl group denotes a phenyl group substituted with the above-mentioned aryl group, and the number of aryl groups is in a range of 1 or more to 5 or less and the kind of them may be the same or different. The carbon number of an aryl group is not particularly limited, being preferably in a range of 6 or more to 12 or less.

An alkyl substituted naphtyl group denotes a naphtyl group substituted with the above-mentioned alkyl group, and the number of alkyl groups is in a range of 1 or more to 7 or less.

An alkoxy substituted naphtyl group denotes a naphtyl group substituted with the above-mentioned alkoxy group, and the number of alkoxy groups is in a range of 1 or more to 7 or less.

An aryl substituted naphtyl group denotes a naphtyl group substituted with the above-mentioned aryl group, and the number of aryl groups is in a range of 1 or more to 7 or less.

An alkyl substituted phenanthryl group denotes a naphtyl group substituted with the above-mentioned alkyl group, and the number of alkyl groups is in a range of 1 or more to 9 or less.

An alkoxy substituted phenanthryl group denotes a phenanthryl group substituted with the above-mentioned alkoxy group, and the number of alkoxy groups is in a range of 1 or more to 9 or less.

An aryl substituted phenanthryl group denotes a phenanthryl group substituted with the above-mentioned aryl group, and the number of aryl groups is in a range of 1 or more to 7 or less.

An anthracene compound represented by the general formula (1) of the present invention has high thin film stability and excellent heat resistance by reason of having an anthracene skeleton and a dibenzofuran skeleton or a dibenzothiophene skeleton as electron-donating fused aromatic in a molecule. Among these, $R^{11}$ to $R^{18}$ of the general formula (2) are at least one selected from among a hydrogen atom, alkyl group, cycloalkyl group, alkoxy group, phenyl group, naphtyl group and heteroaryl group, so that thin film stability is improved to thereby allow a light emitting device having high luminous efficiency and excellent durability.

In an anthracene compound represented by the general formula (1), $R^9$ is preferably a substituent represented by the general formula (2) in view of availability of raw materials and ease of synthesis. In addition, X of the general formula (2) is preferably an oxygen atom by reason of allowing higher luminous efficiency.

In addition, at least one of substituents except the general formula (2) introduced to $R^1$ to $R^{10}$ of the general formula (1), or at least one of substituents introduced to $R^{11}$ to $R^{18}$ of the general formula (2) is preferably an electron-donating substituent in view of charge transport property and durability. Examples preferably used for an electron-donating substituent include alkyl groups such as a methyl group and tert-butyl group, alkoxy groups such as a methoxy group, and heteroaryl groups such as furan, benzofuran, dibenzofuran, thiophene, benzothiophene, dibenzothiophene, pyrrole, indole and carbazole.

An anthracene compound represented by the general formula (3) of the present invention has high thin film stability and excellent heat resistance by reason of having an anthracene skeleton and a carbazole skeleton as electron-donating fused aromatic in a molecule, and linking the anthracene skeleton and the carbazole skeleton through a heteroarylene group or arylene group with a carbon number of 6 to 12. Here, any one of $R^{19}$ to $R^{27}$ and any one of $R^{28}$ to $R^{37}$ are used for linking with A; $R^{19}$ and $R^{36}$ or $R^{37}$ are preferably used for linking with A in view of availability of raw materials and ease of synthesis.

In the general formula (3), it is preferable in view of charge transport property and thin film stability that A is a phenylene group having no substituents, phenylene group substituted with a group selected from among an alkyl group with a carbon number of 1 or more to 6 or less and an alkoxy group with a carbon number of 1 or more to 6 or less, naphthylene group having no substituents, or naphthylene group substituted with a group selected from among an alkyl group with a carbon number of 1 or more to 6 or less and an alkoxy group with a carbon number of 1 or more to 6 or less, that $R^{36}$ or $R^{37}$ is selected from among a phenyl group having no substituents, alkyl substituted phenyl group, alkoxy substituted phenyl group, aryl substituted phenyl group, naphtyl group having no substituents, alkyl substituted naphtyl group and alkoxy substituted naphtyl group, and that at least one of $R^{29}$, $R^{30}$, $R^{33}$ and $R^{34}$ is substituted with an alkyl group with a carbon number of 1 to 6.

An anthracene compound represented by the general formula (1) or (3) of the present invention is excellent in amorphous thin film-forming properties and heat resistance, so that the use of them as a light emitting device material allows a light emitting device having high luminous efficiency and excellent durability.

An anthracene compound represented by the general formula (1) or (3) as described above is not particularly limited; specific examples thereof include the following.

[Chemical formula 7]

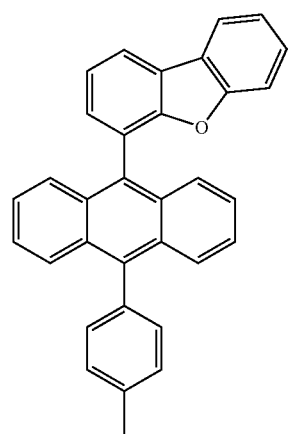

[1]

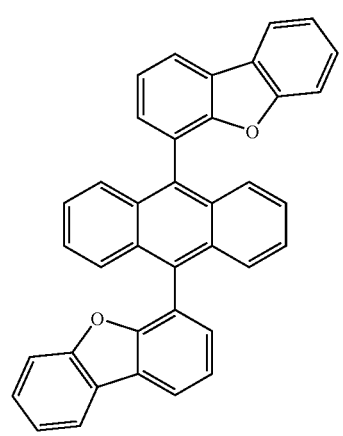

[2]

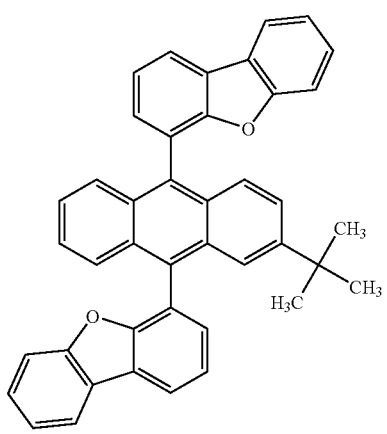
[3]
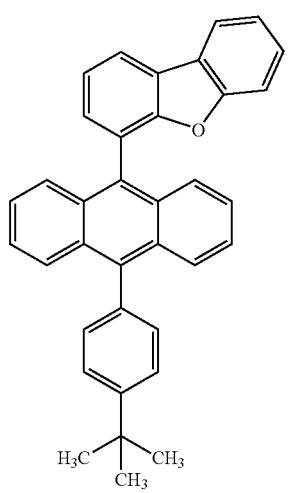
[4]
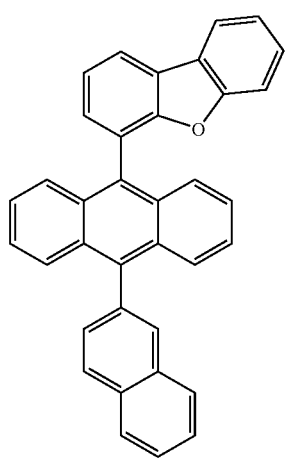
[5]
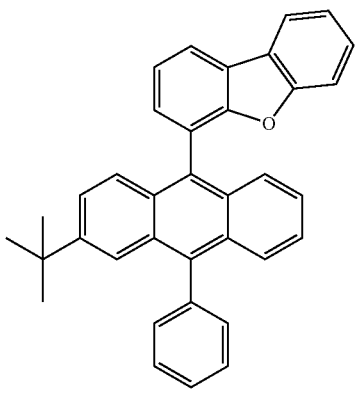
[6]
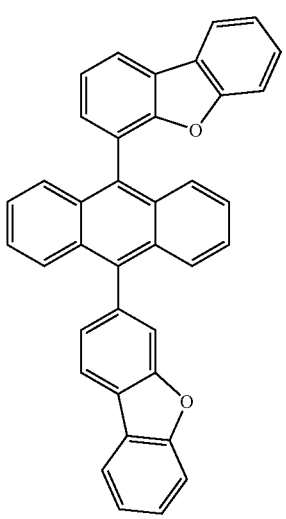
[7]
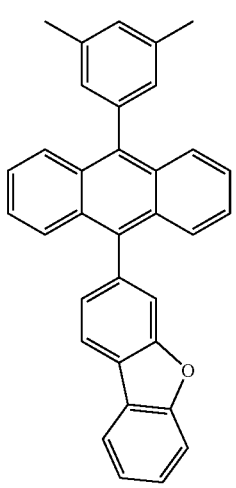
[8]

[9]
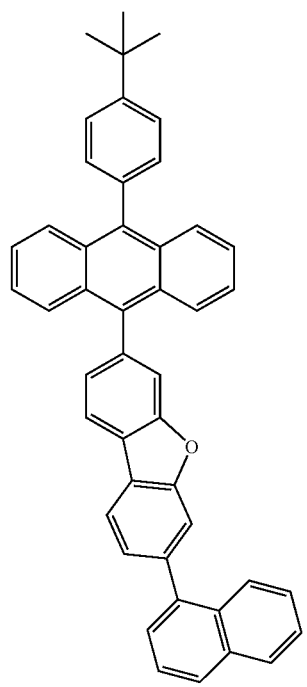
[10]
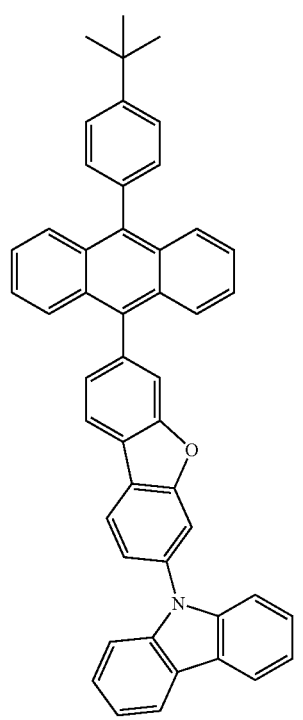
[11]
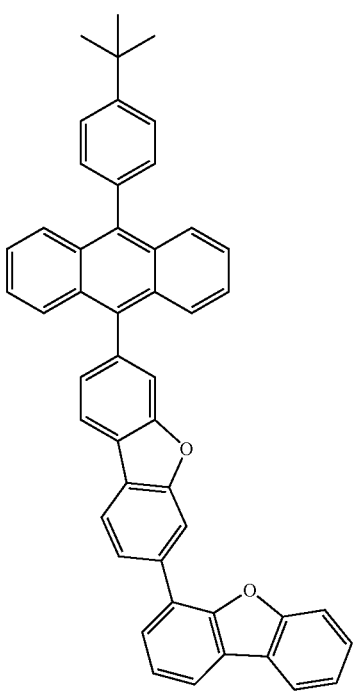
[12]
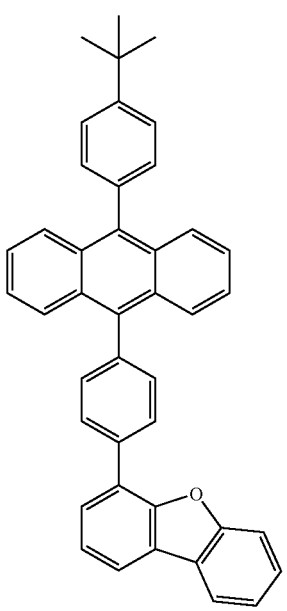

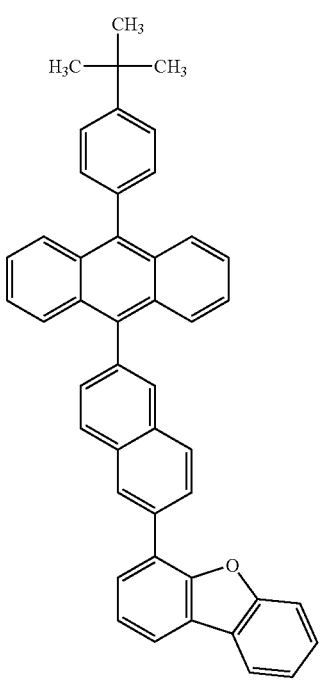
[13]
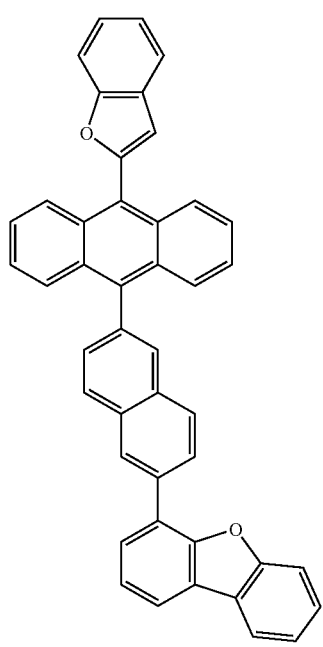
[15]
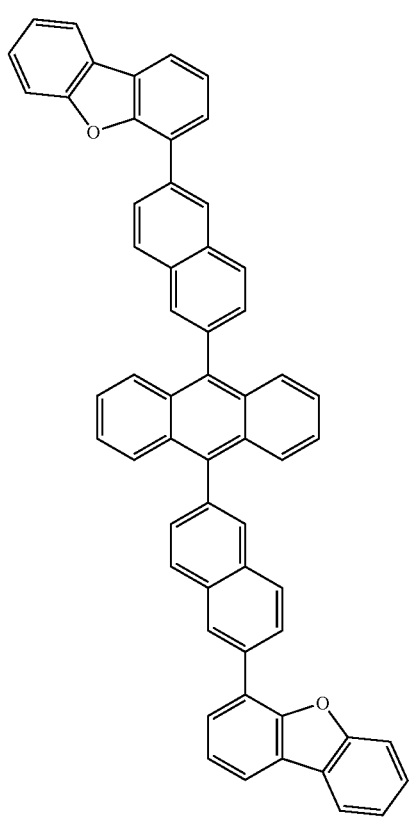
[14]
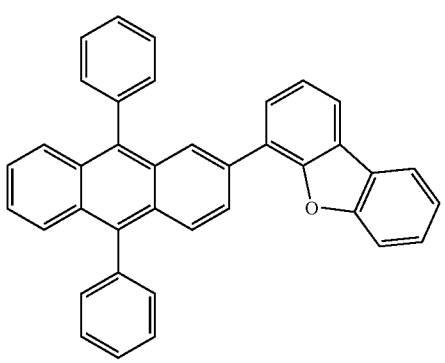
[16]
[17]

[18] 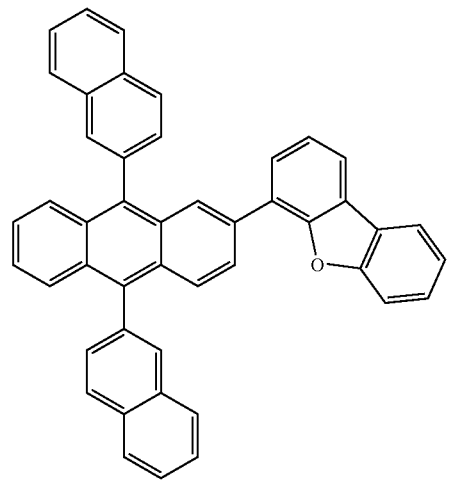
[19] 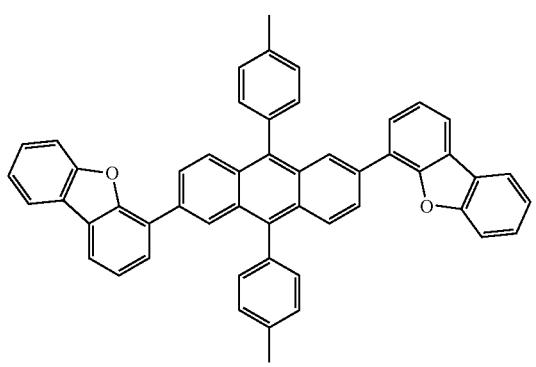
[20] 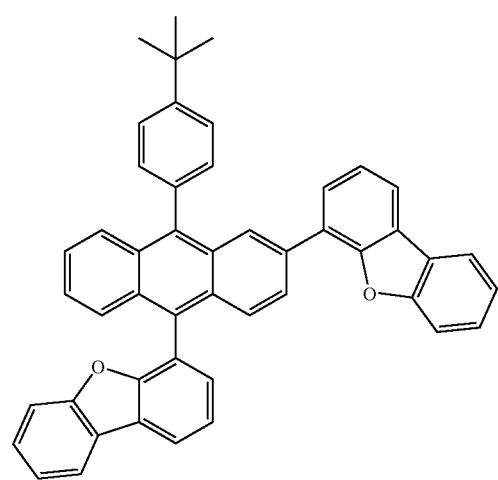
[21] 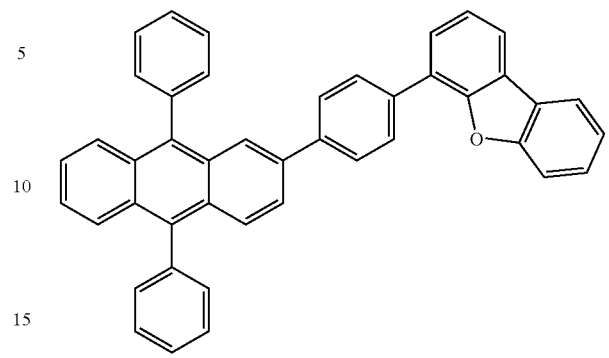
[22] 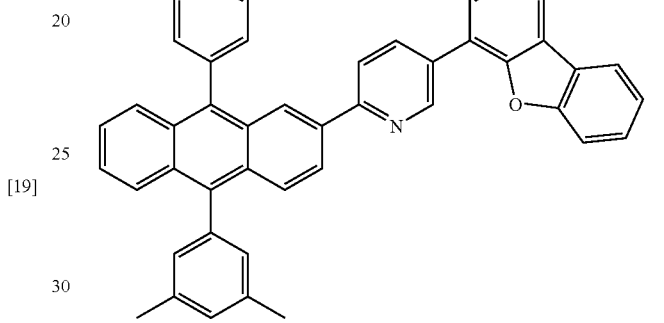
[23] 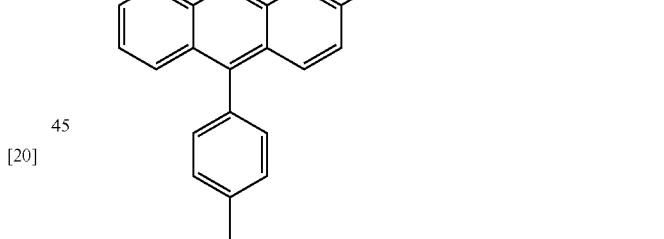
[24] 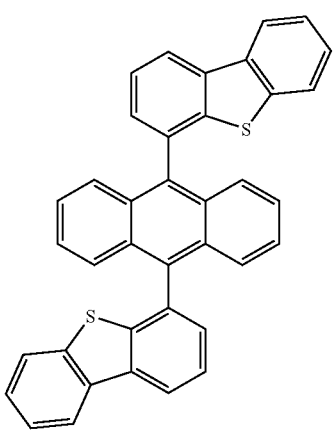

[25] 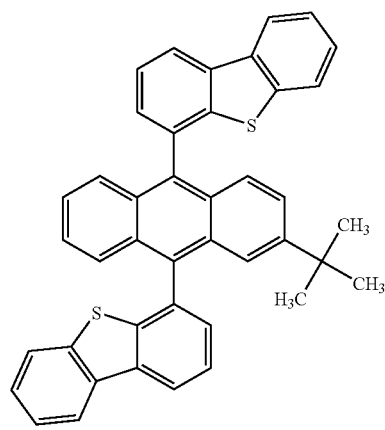
[26] 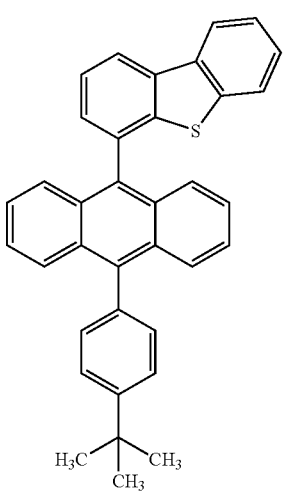
[27] 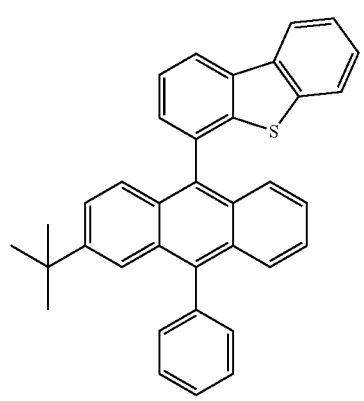
[28] 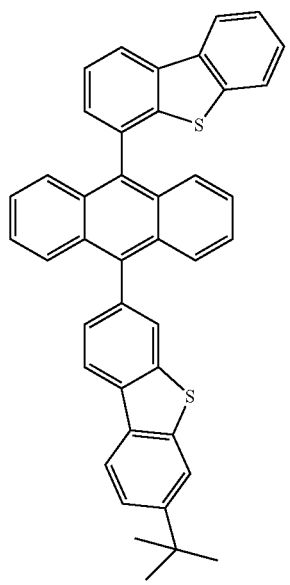
[29] 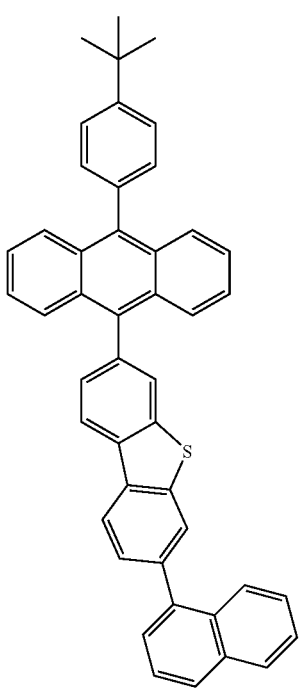

[Chemical formula 11]
[30]
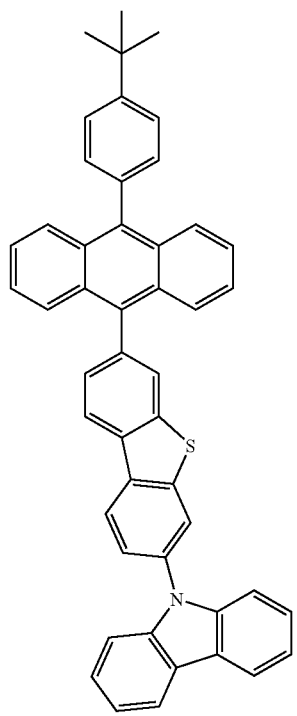
[31]
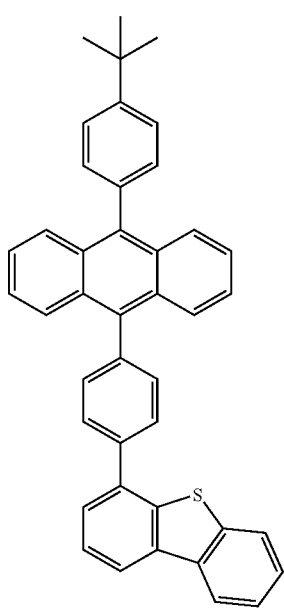
[32]
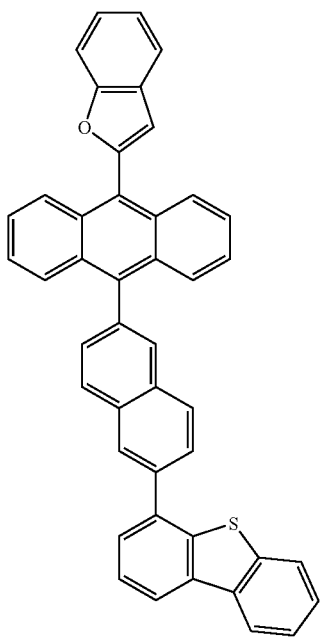
[33]
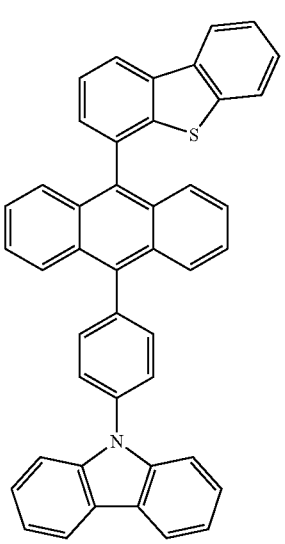

[34]
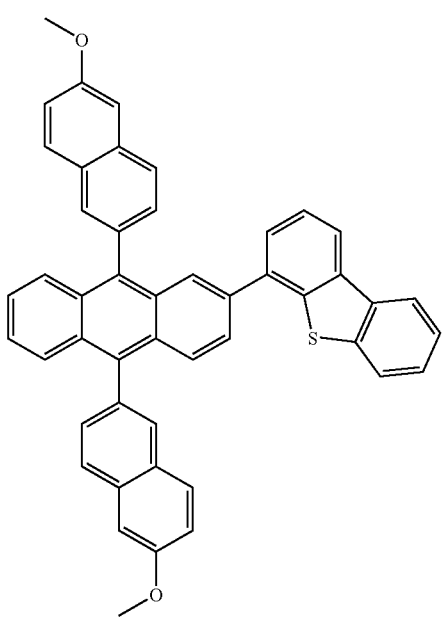
[35]
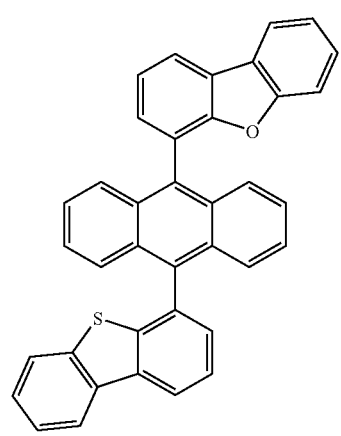
[36]
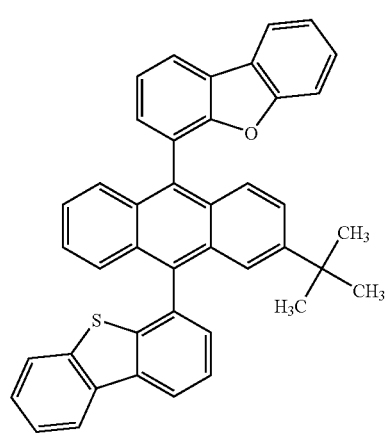
[37]
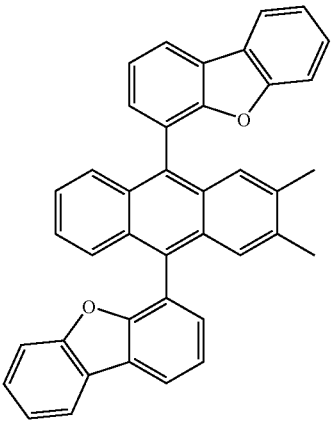
[38]
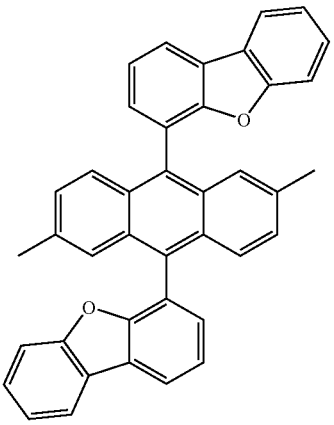
[Chemical formula 12]
[39]
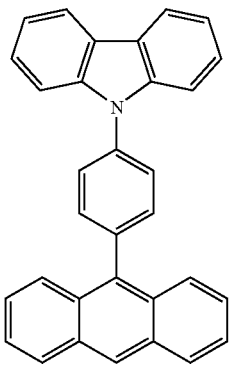
[40]
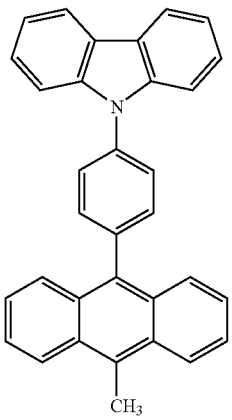

[41]
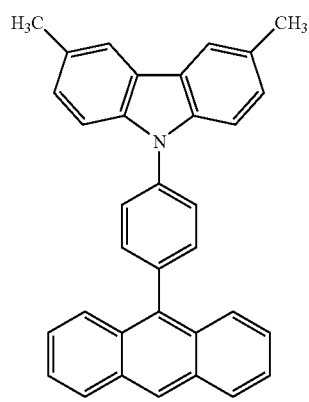
[42]
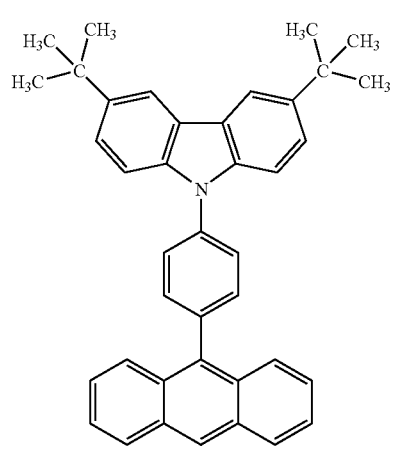
[43]
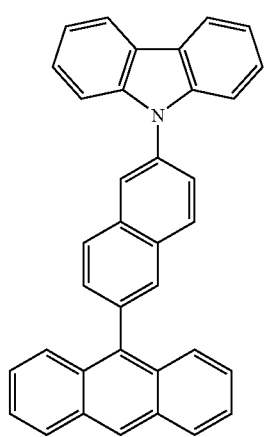
[44]
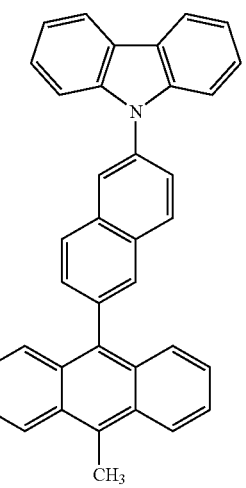
[45]
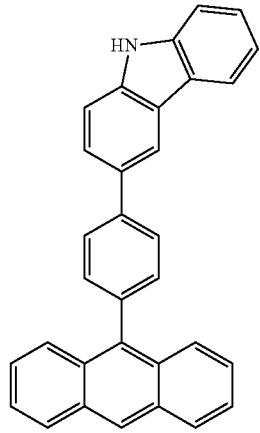
[46]

[47]
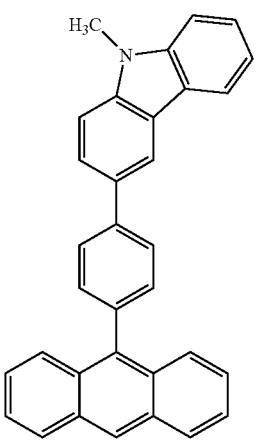
[48]
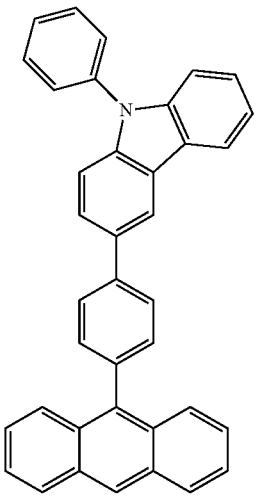
[49]
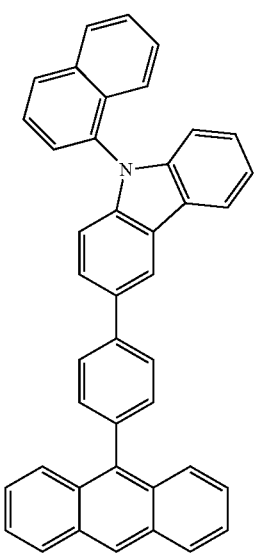
[50]
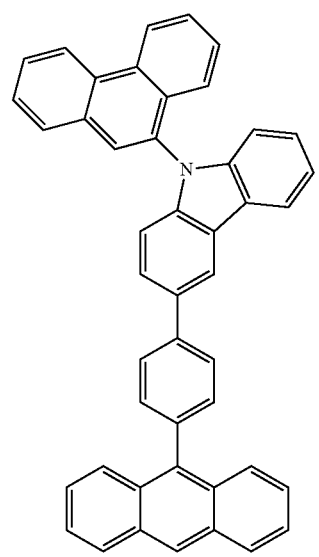
[51]
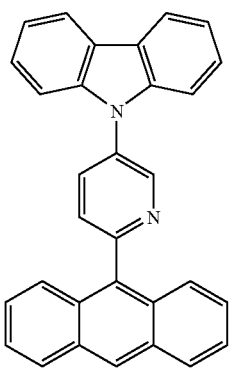
[52]
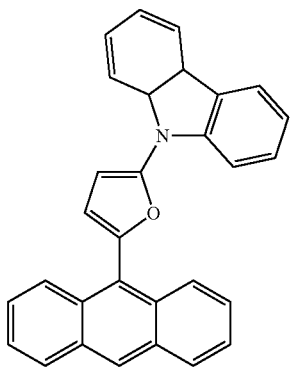
[53]
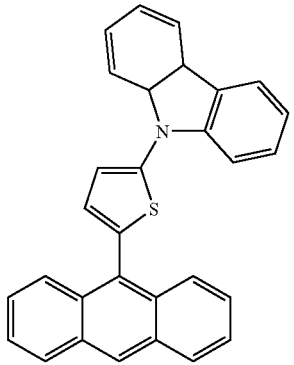

[54]
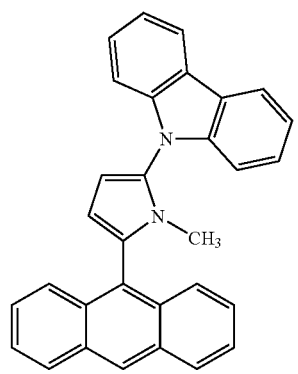
[Chemical formula 13]
[55]
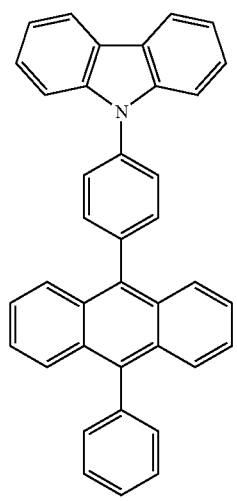
[56]
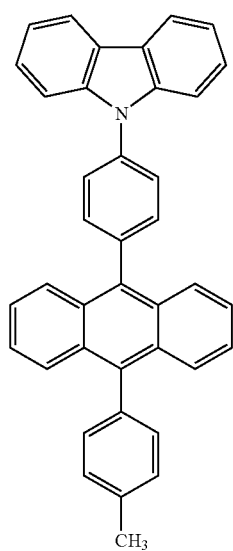
[57]
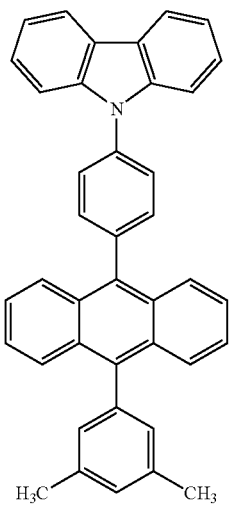
[58]
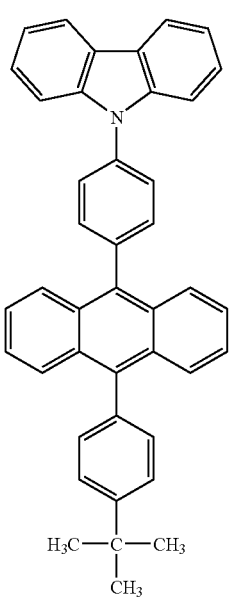
[59]
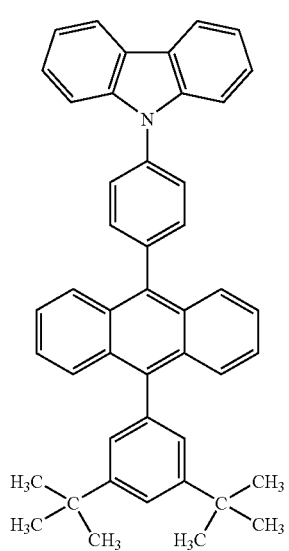

-continued
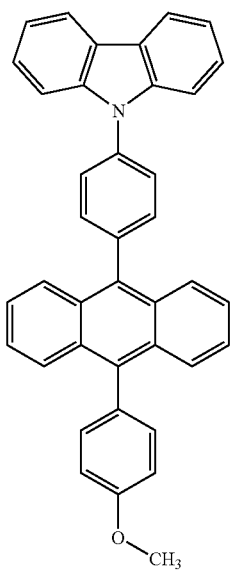
[60]
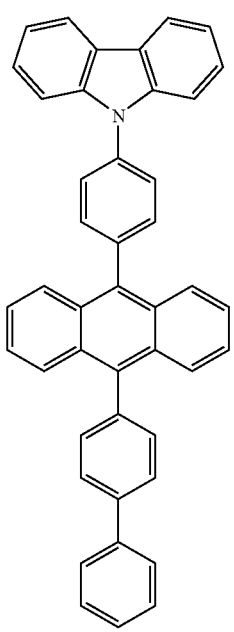
[61]
-continued
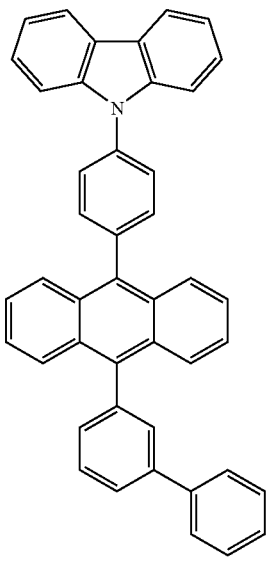
[62]
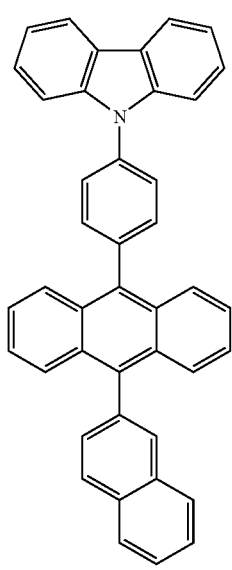
[63]

31
-continued
[64]
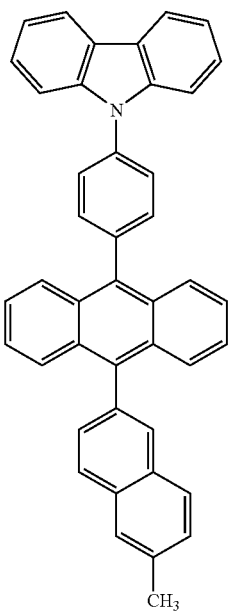
[65]
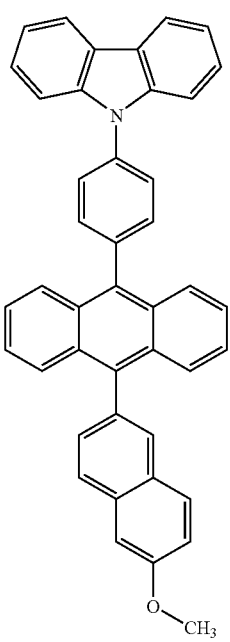
32
-continued
[66]
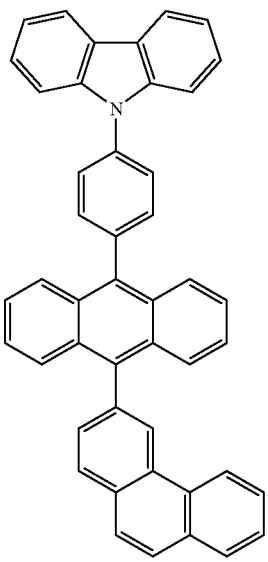
[Chemical formula 14]
[67]
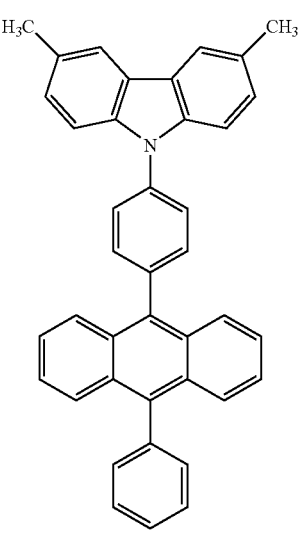

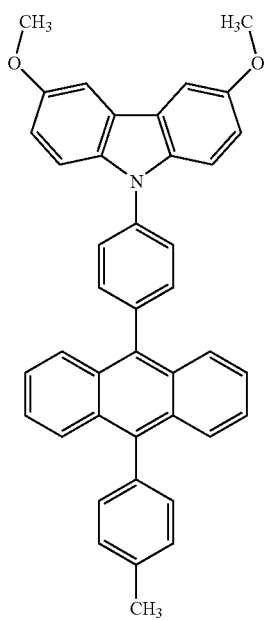
[68]
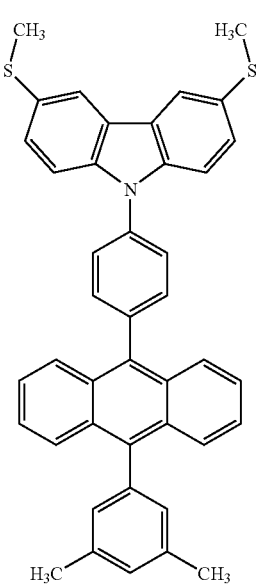
[69]
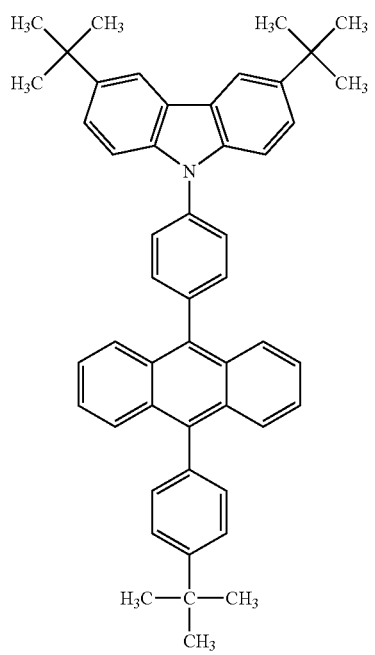
[70]
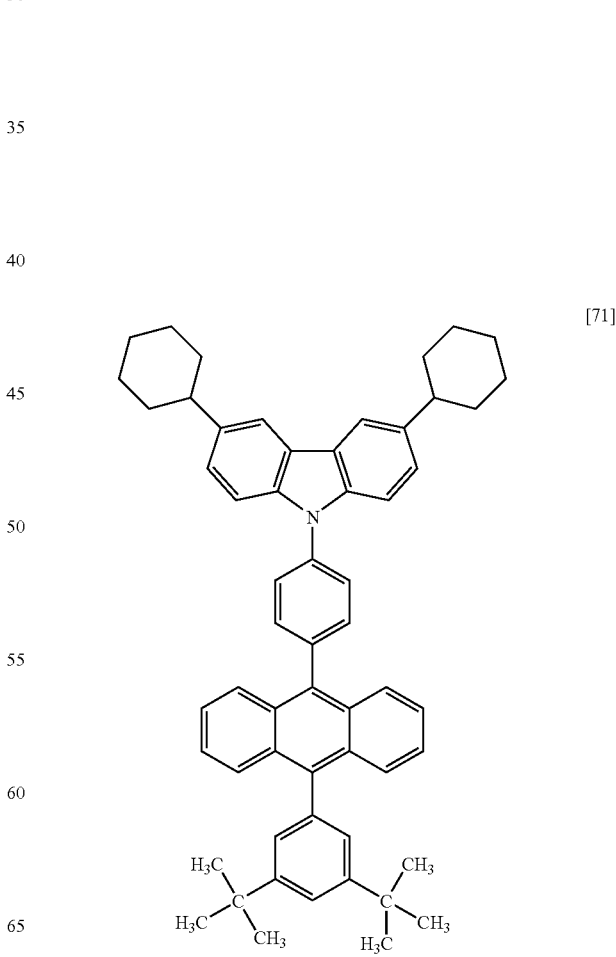
[71]

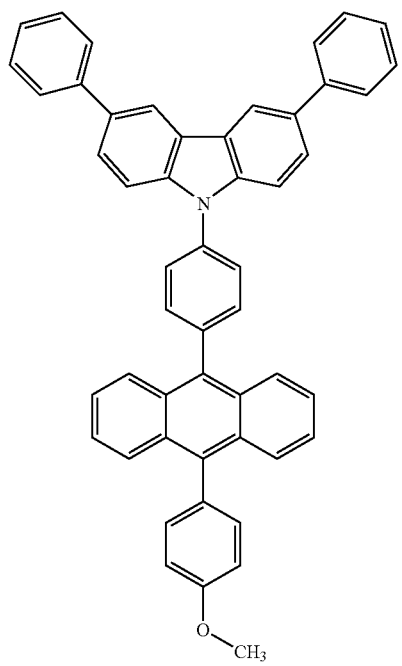
[72]
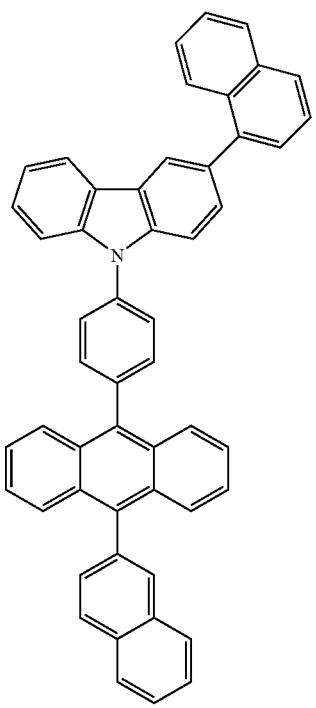
[74]
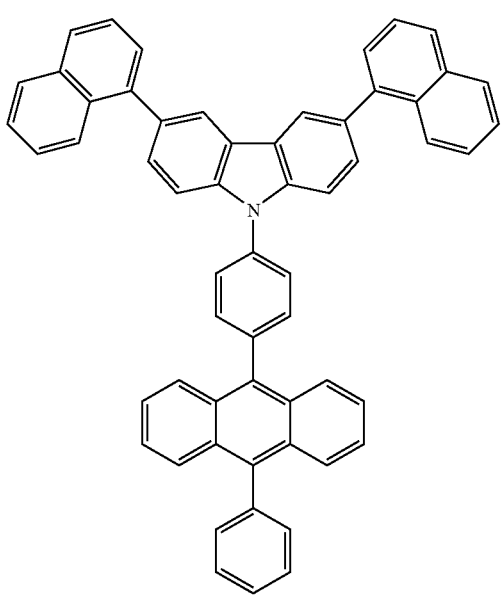
[73]
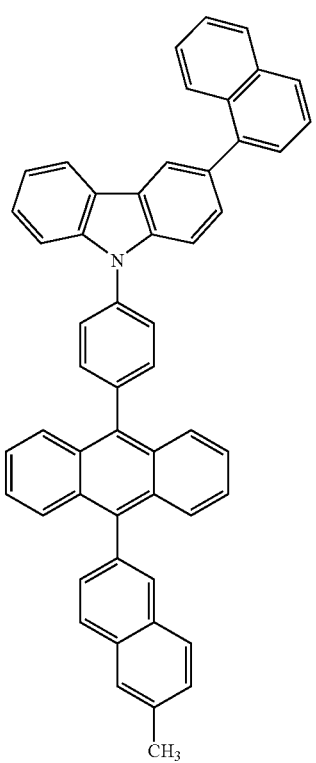
[75]

[Chemical formula 15]
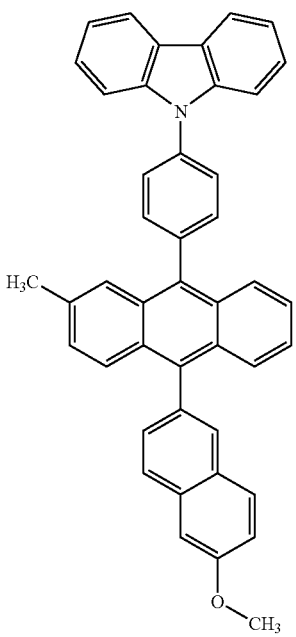
[76]
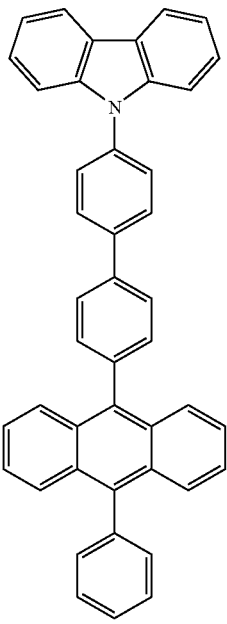
[78]
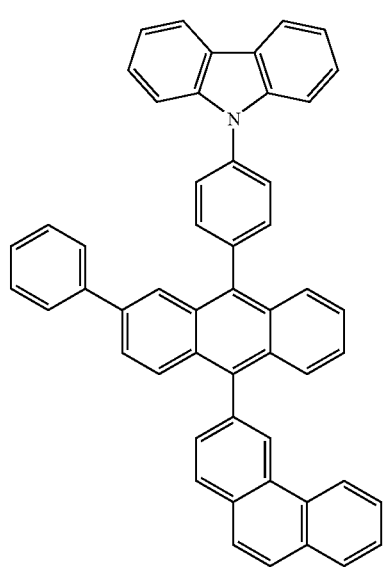
[77]
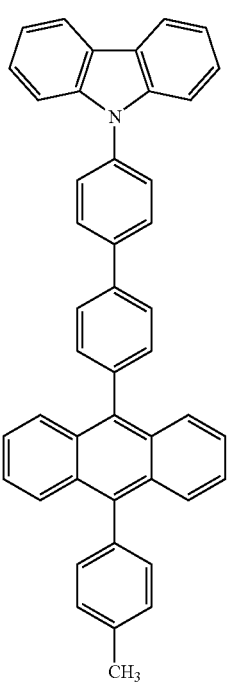
[79]

[80]
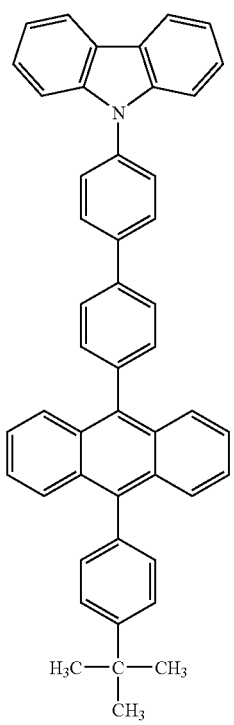
[82]
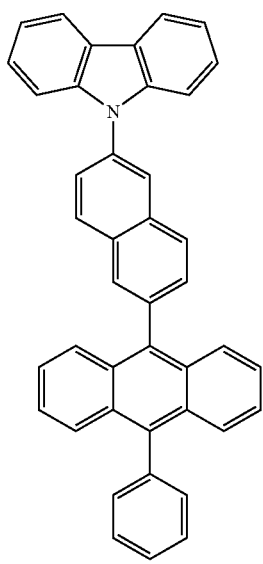
[81]
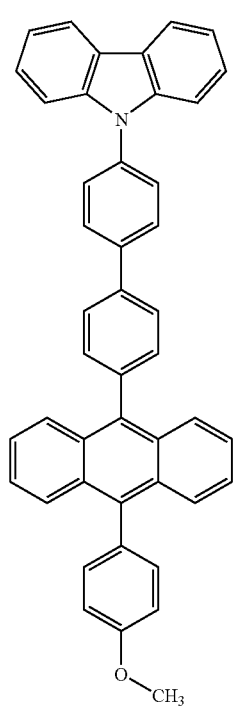
[83]
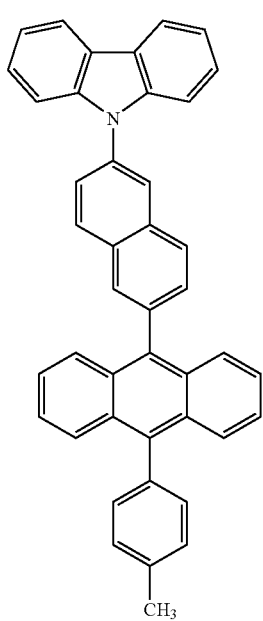

[84]
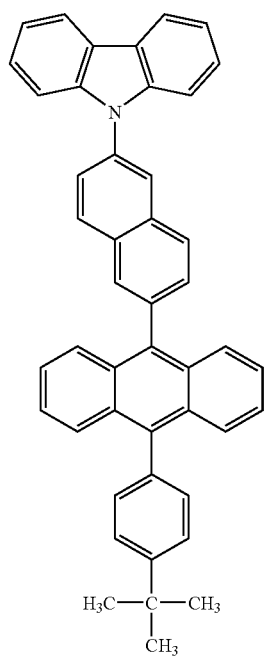
[85]
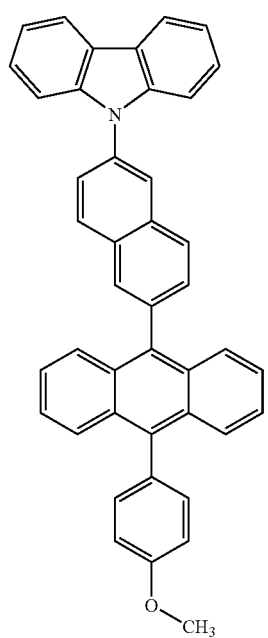
[Chemical formula 16]
[86]
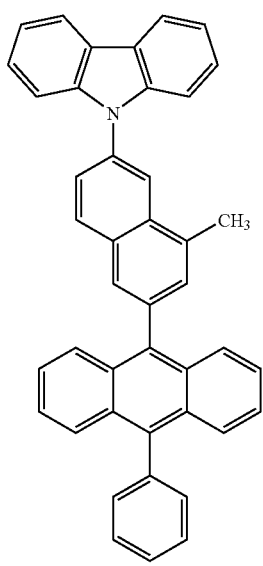
[87]
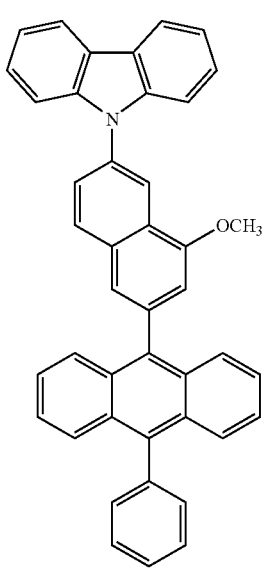
[88]
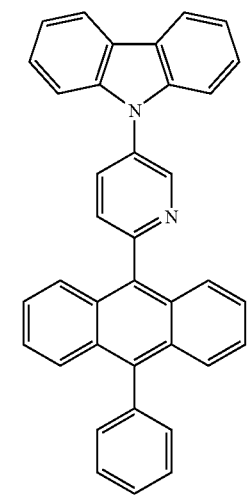

[89]
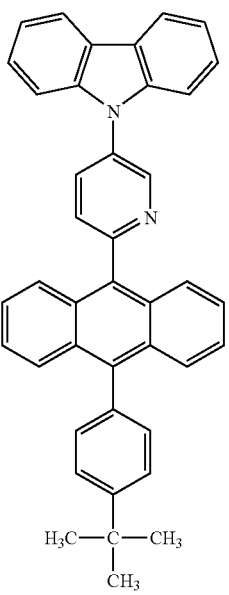
[90]
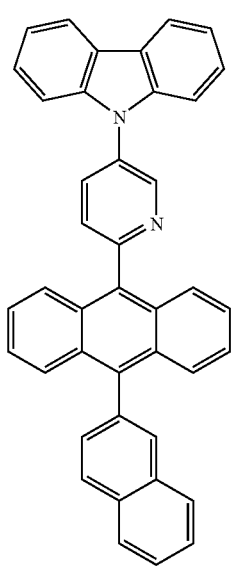
[91]
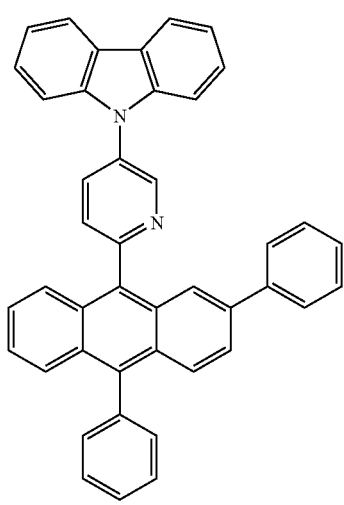
[92]
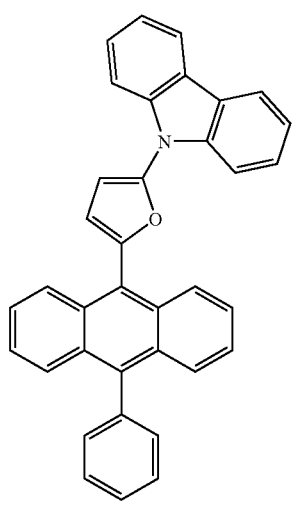
[93]
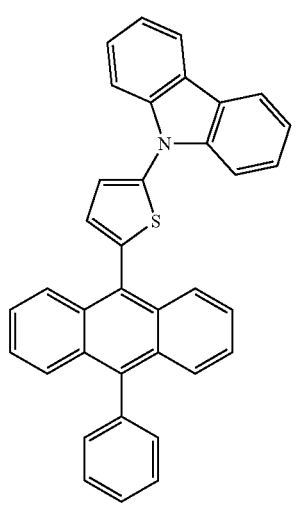
[94]
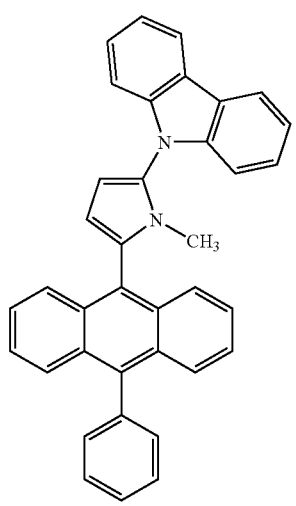

[95]
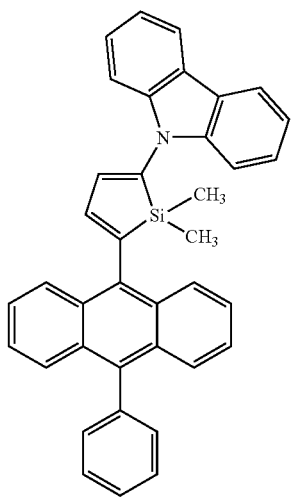
[96]
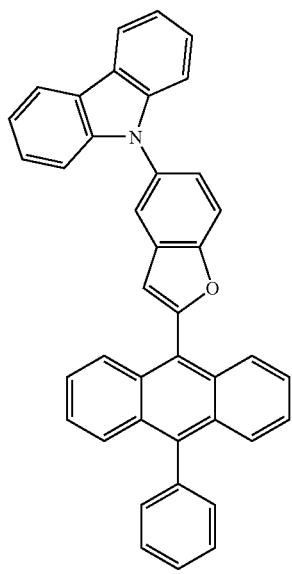
[97]
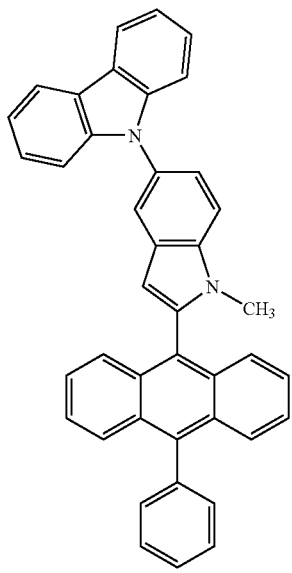
[98]
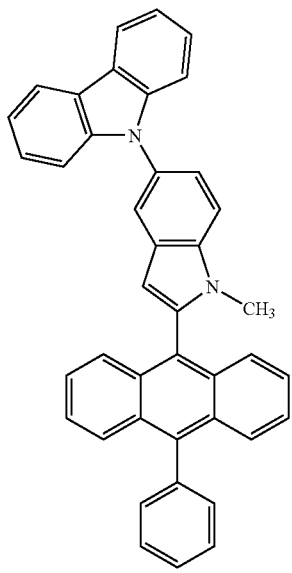
[99]
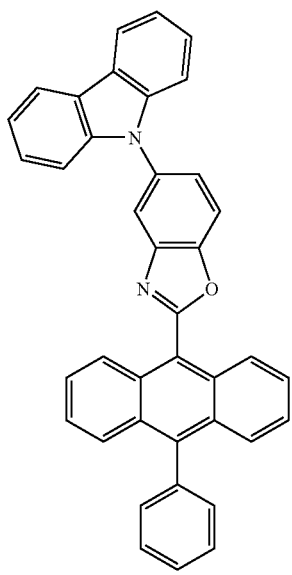
[Chemical formula 17]
[100]
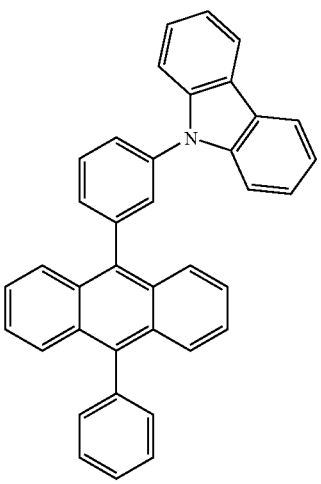

[101]
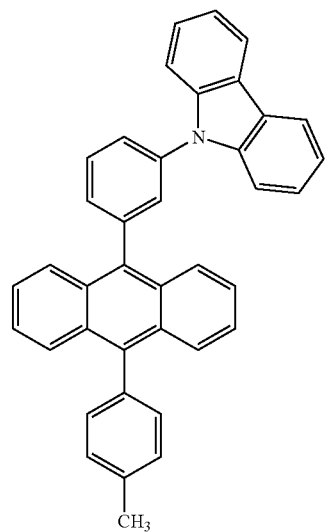
[102]
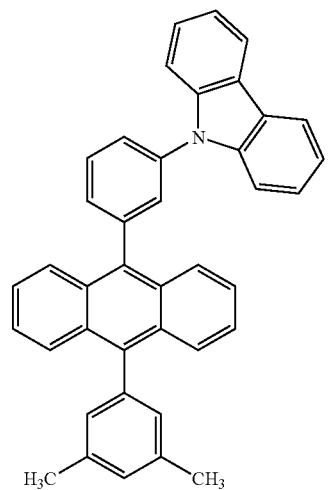
[103]
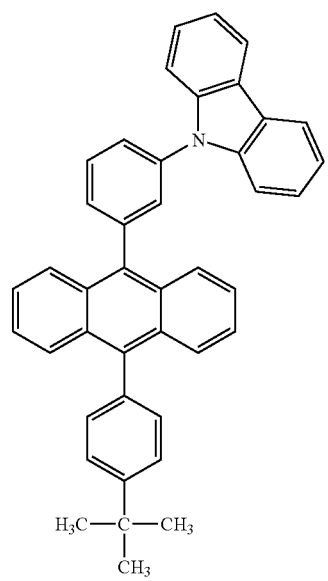
[104]
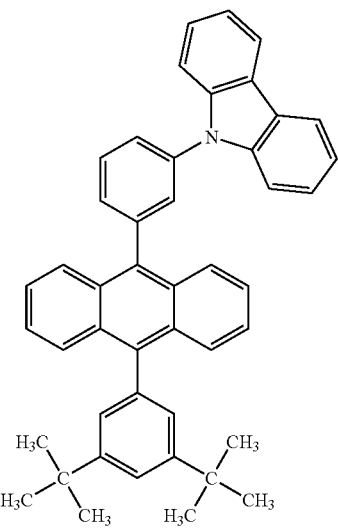
[105]
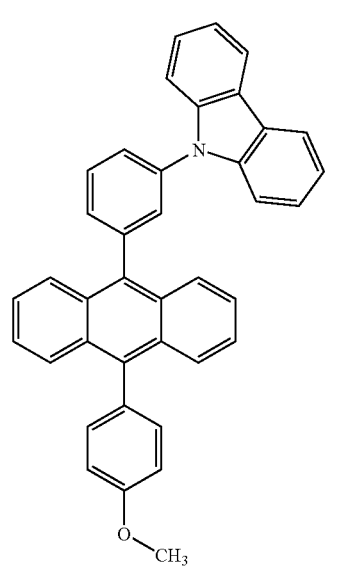

-continued
[106]
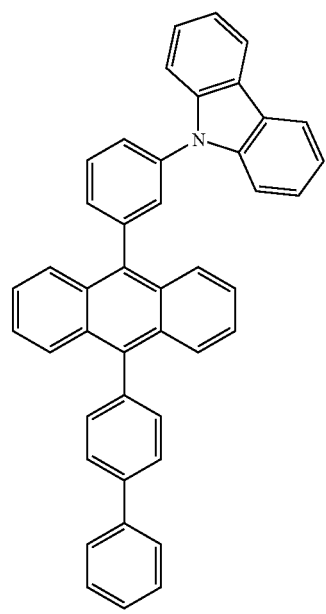
[107]
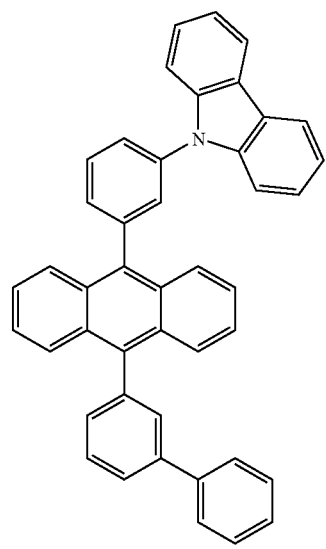
-continued
[108]
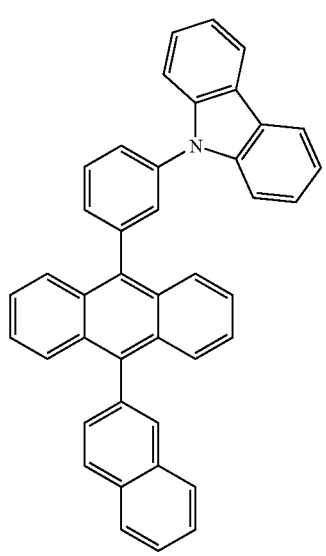
[109]
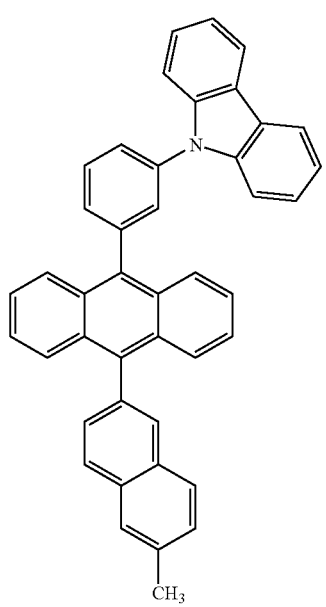

[Chemical formula 18]
[110] 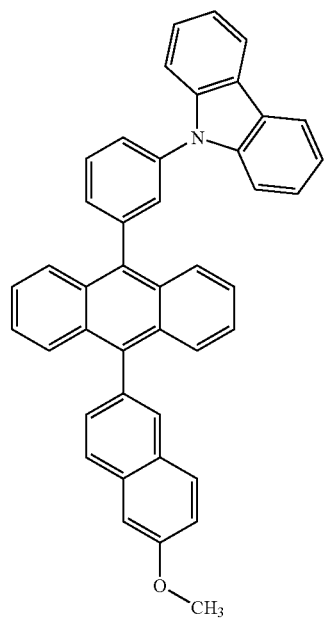
[111] 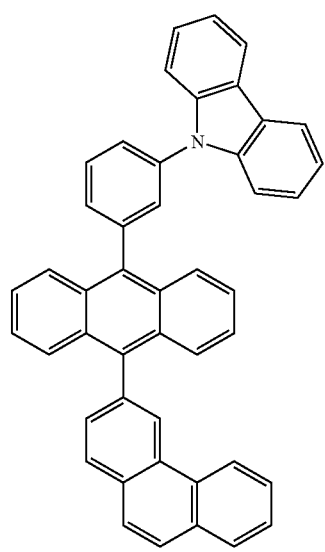
[112] 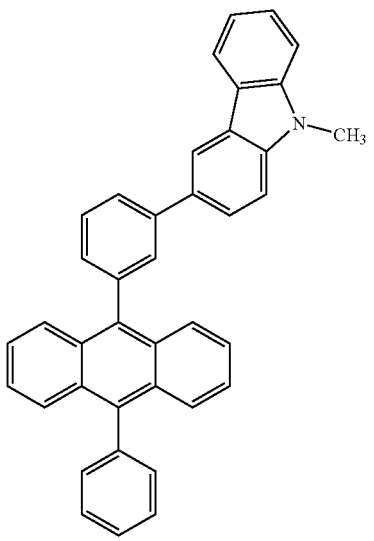
[113] 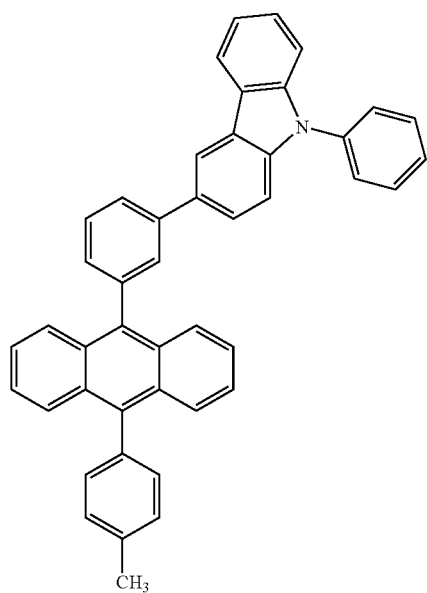

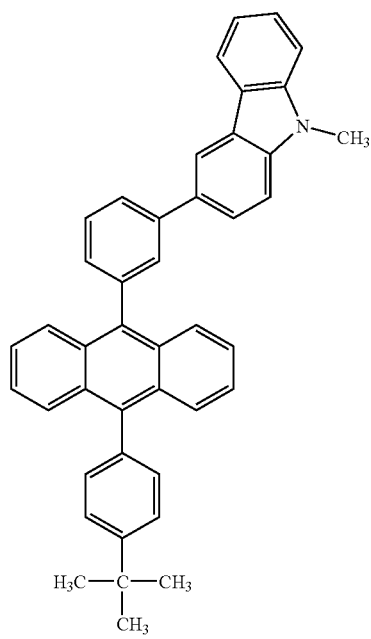
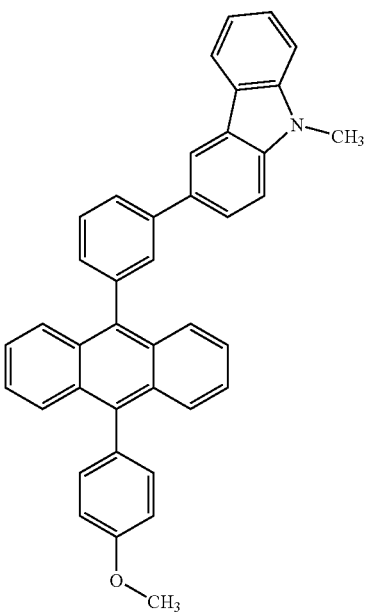
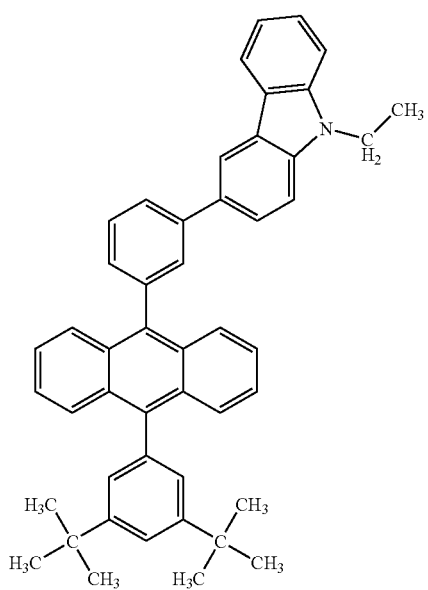
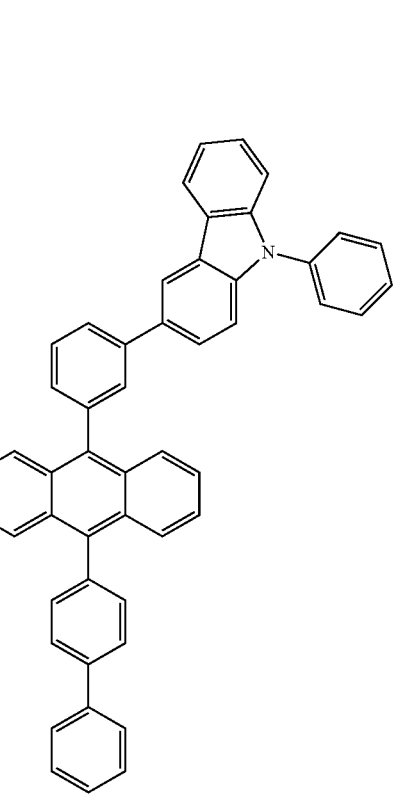

-continued
[118]
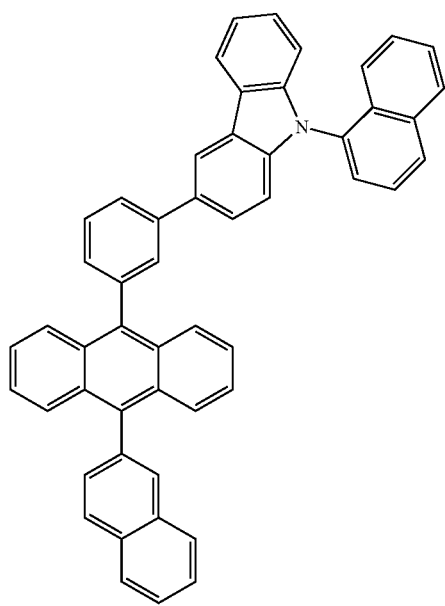
[119]
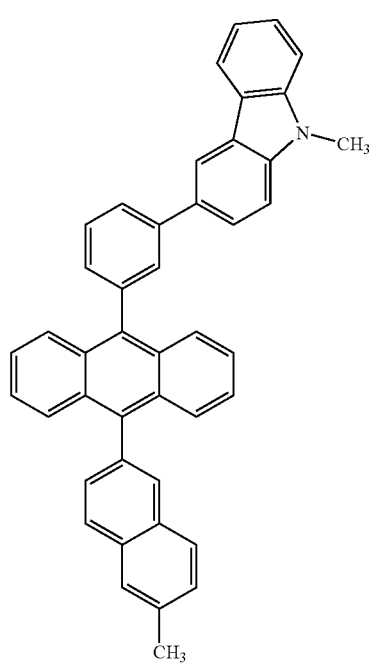
-continued
[120]
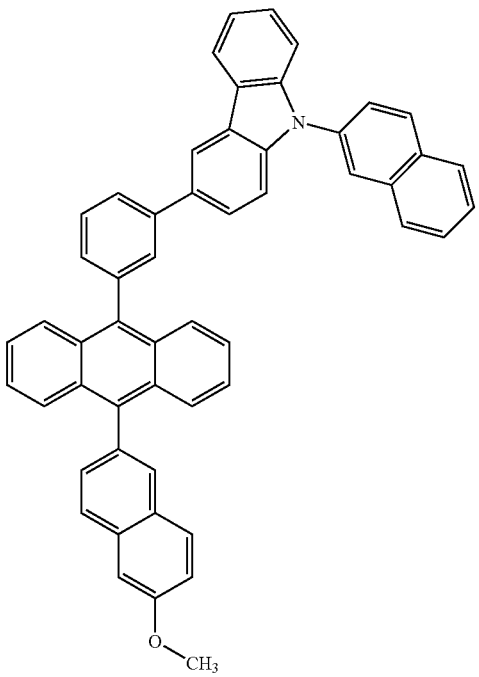
[Chemical formula 19]
[121]
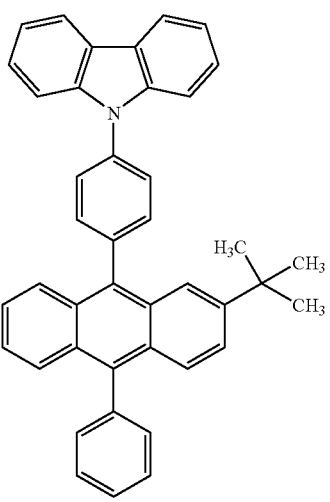

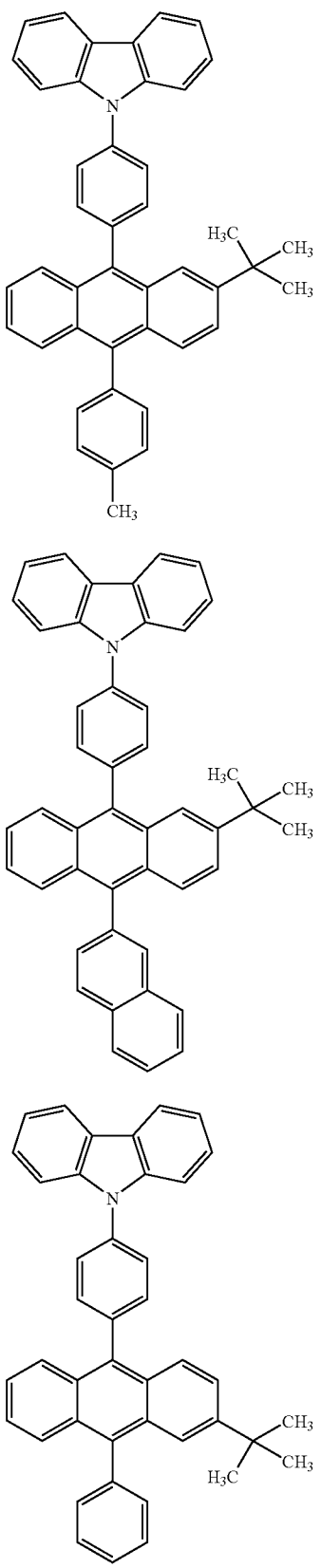
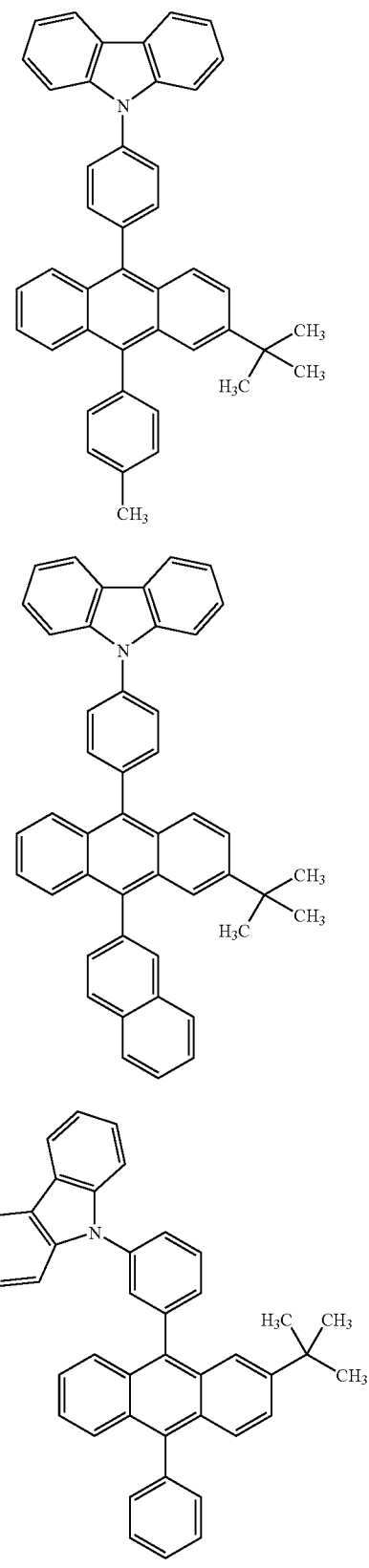

[128]
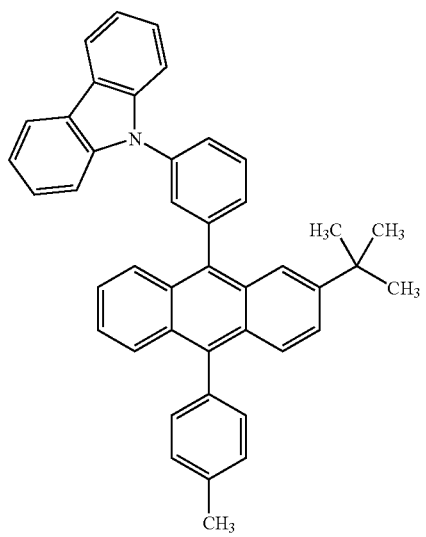
[129]
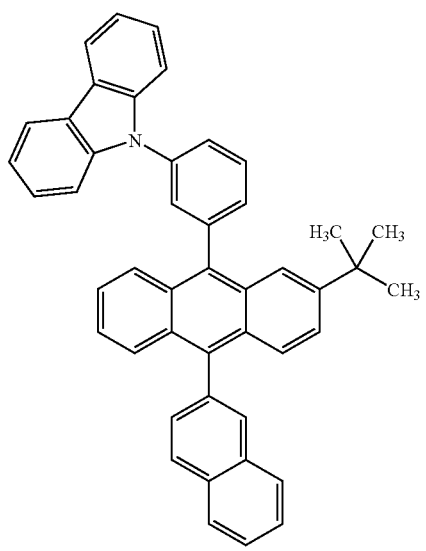
[130]
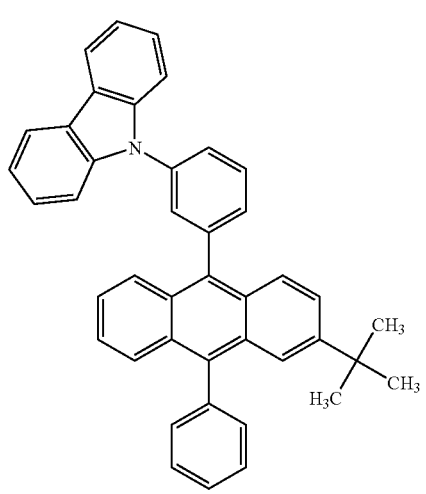
[131]
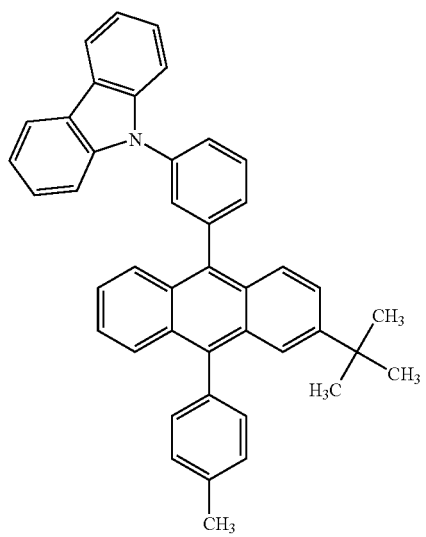
[132]
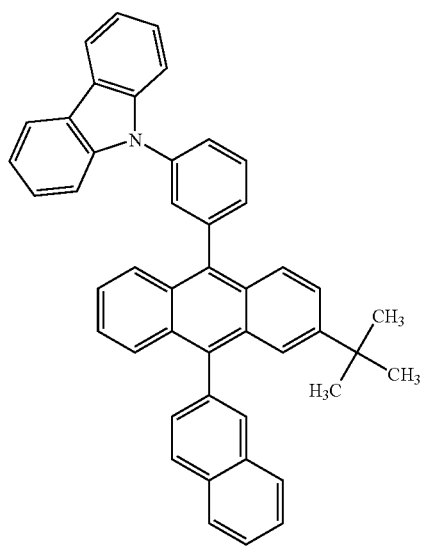
[Chemical formula 20]
[133]
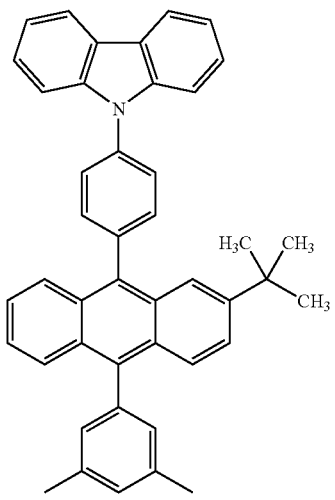

[134]
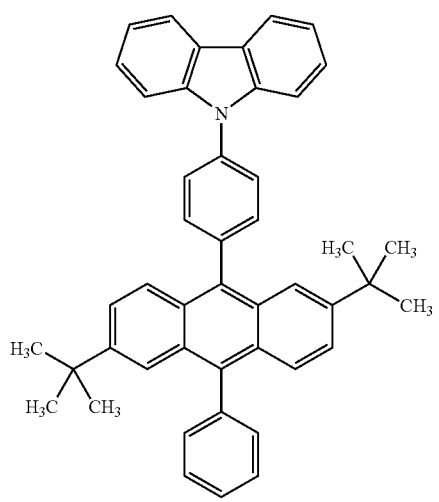
[135]
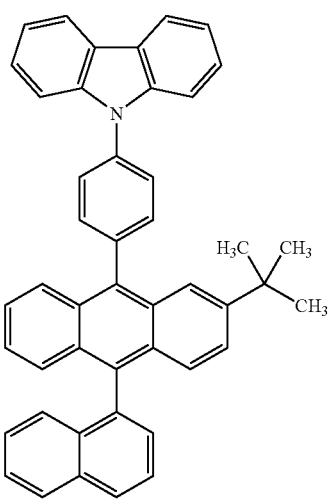
[136]
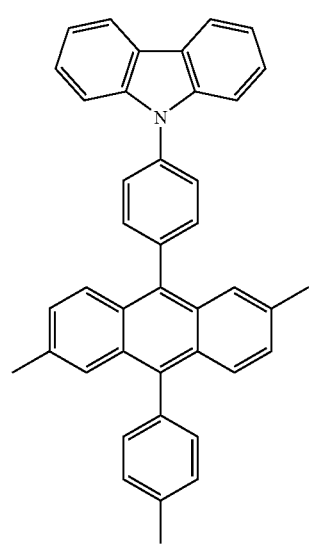
[137]
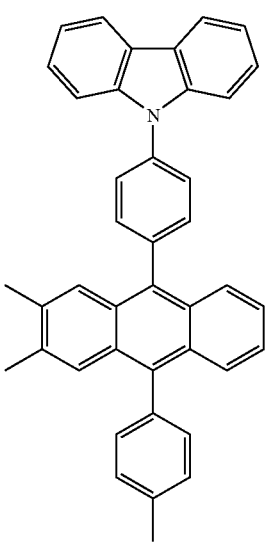
[138]
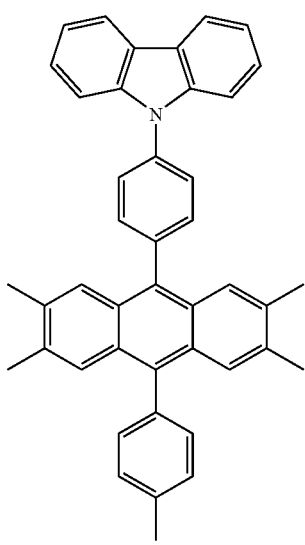
[139]
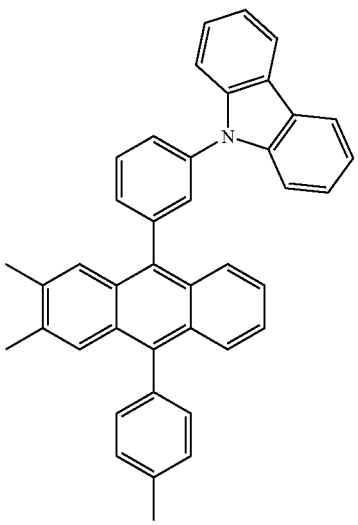

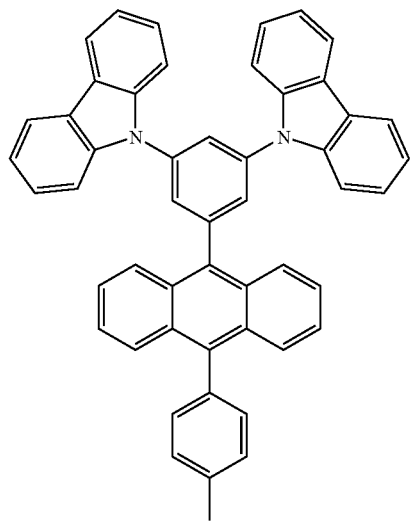
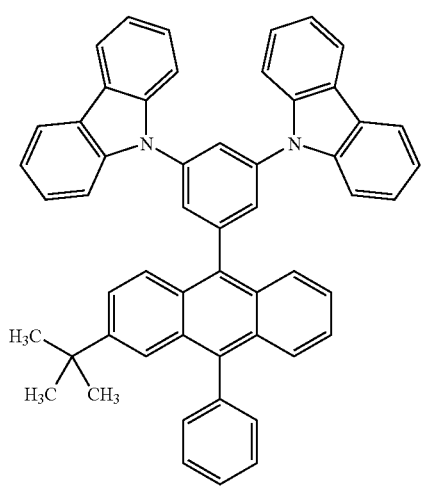
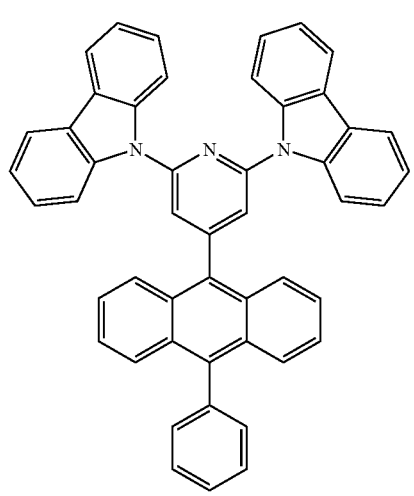
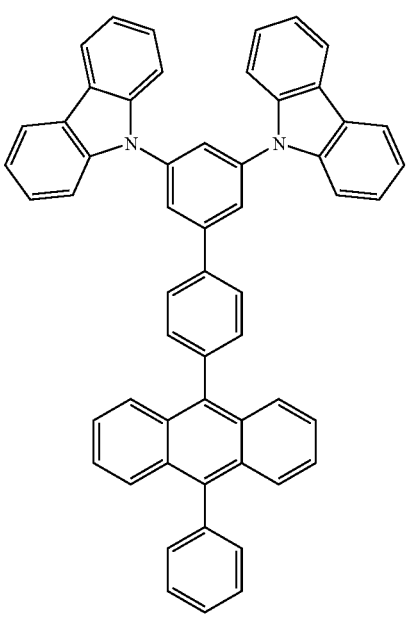
[Chemical formula 21]
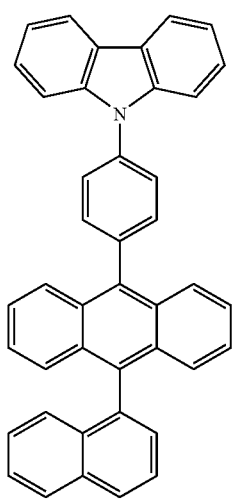
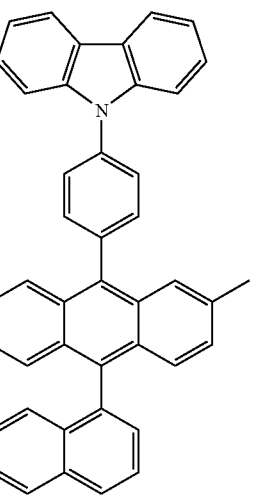

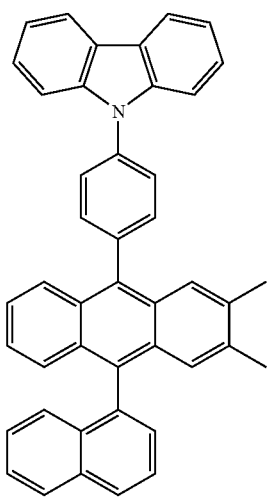
[146]
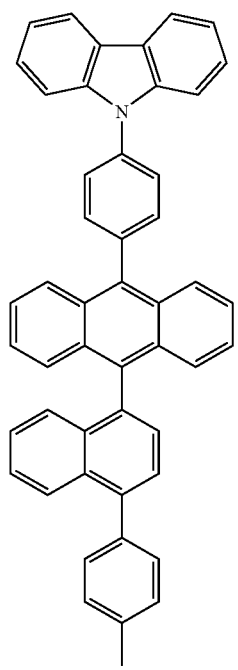
[148]
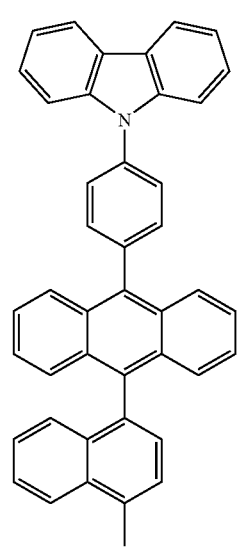
[147]
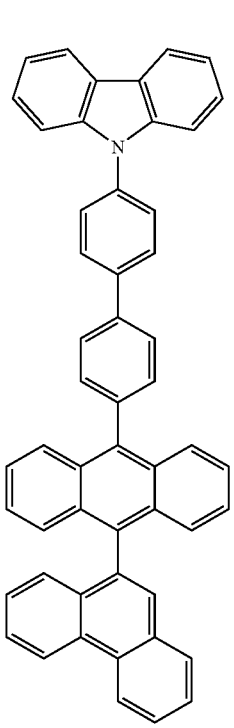
[149]

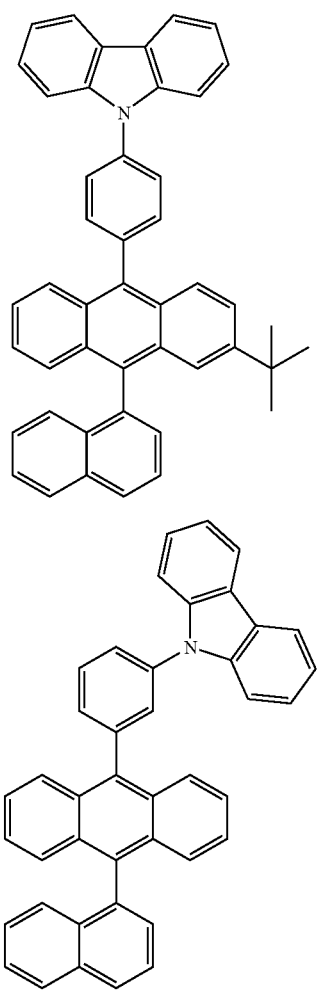

A known method can be used for synthesizing an anthracene compound represented by the general formula (1) or (3). Examples of a method of introducing an aryl group or heteroaryl group to an anthracene skeleton include a method of using a coupling reaction of halogenated anthracene and aryl or heteroaryl metal reagent under palladium catalyst and nickel catalyst, and a method of using a dehydration condensation reaction of acetyl group substituted anthracene and aromatic amino aldehyde, which examples are not limited thereto. Examples of a method of introducing an arylcarbazolyl group to an anthracene skeleton include a method of using a coupling reaction of halogenated anthracene and arylcarbazoleboronic acid under palladium catalyst and nickel catalyst, and a coupling reaction of anthraceneboronic acid and halogenated arylcarbazole under palladium catalyst and nickel catalyst; and a method of using a coupling reaction with carbazole under palladium catalyst and copper catalyst after introducing a halogenated aryl group to an anthracene skeleton.

Next, an embodiment of a light emitting device in the present invention is explained in detail by referring to examples. A light emitting device of the present invention is composed of at least an anode, a cathode and an organic layer made of a light emitting device material interposing between the anode and the cathode.

The anode used in the present invention is not particularly limited if a material capable of efficiently injecting a hole into the organic layer, and a material with comparatively high work function is preferably used; examples thereof include conductive metal oxides such as tin oxide, indium oxide, indium zinc oxide and indium tin oxide (ITO), metals such as gold, silver and chrome, inorganic conductive materials such as copper iodide and copper sulfide, or conductive polymers such as polythiophene, polypyrrole and polyaniline. These electrode materials may be used singly or in plurality by lamination or mixture.

The resistance of the anode is preferred to supply current sufficient for light emission of a light emitting device, and low resistance is desirable in view of power consumption of a light emitting device. For example, an ITO substrate of 300 Ω/square or less functions as a device electrode, and the use of a low-resistance product of 100 Ω/square or less is particularly desirable for the reason that a substrate of approximately 10 Ω/square can presently be supplied. The thickness of ITO can optionally be selected in accordance with resistance values and is frequently used between typically 100 to 300 nm.

In order to retain mechanical strength of a light emitting device, a light emitting device is preferably formed on a substrate. Glass substrates such as soda glass and non-alkali glass are appropriately used for the substrate. The thickness of the glass substrate is preferred to be sufficient for retaining mechanical strength, that is, 0.5 mm or more. With regard to materials for glass, non-alkali glass is preferable for the reason that less ion dissolution from glass is preferable, and soda-lime glass on which barrier coat such as $SiO_2$ is applied is also commercially available and thereby can be used. In addition, if the anode functions stably, the substrate need not be glass; for example, the anode may be formed on a plastic substrate. A method of forming an ITO film is not particularly limited, such as an electron beam method, sputtering method and chemical reaction method.

Materials used for the cathode used in the present invention are not particularly limited if a substance capable of efficiently injecting an electron into the organic layer, examples thereof generally including platinum, gold, silver, copper, iron, tin, zinc, aluminum, indium, chromium, lithium, sodium, potassium, cesium, calcium and magnesium, and alloys thereof. In order to improve device performance by increasing electron injection efficiency, lithium, sodium, potassium, cesium, calcium, magnesium or alloys containing these low work function metals are effective. However, generally, these low work function metals are frequently unstable in the atmosphere, so that preferable examples include a method of obtaining an electrode having high stability by doping the organic layer with a very small amount of lithium and magnesium (1 nm or less at indication of a film thickness meter for vacuum deposition). An inorganic salt such as lithium fluoride can be used. In addition, preferable examples for protection of an electrode include laminating of metals such as platinum, gold, silver, copper, iron, tin, aluminum and indium or alloys using these metals, inorganic matter such as silica, titania and silicon nitride, and organic polymeric compounds such as polyvinyl alcohol, polyvinyl chloride and hydrocarbon polymeric compound. A method of producing these electrodes is not particularly limited if continuity can be secured, such as resistance heating, electron beam, sputtering, ion plating and coating.

With regard to a light emitting device of the present invention, an organic layer is formed from a light emitting device material containing an anthracene compound represented by the general formula (1) or (3). A light emitting device material corresponds to either of an object which emits for itself and an object which assists light emission thereof, and signifies a compound involved in light emission, specifically corresponding to a hole transporting material, luminescent material and electron transporting material.

The organic layer composing a light emitting device of the present invention is composed of a luminescent layer having at least a light emitting device material. Composition examples of the organic layer include a composition consisting of only the luminescent layer as well as laminated compositions such as 1) hole transporting layer/luminescent layer/electron transporting layer, 2) luminescent layer/electron transporting layer and 3) hole transporting layer/luminescent layer. Each of the above-mentioned layers may be either of a monolayer and a multilayer. In the case where the hole transporting layer and the electron transporting layer have a multilayer, layers thereof on the side contacting with an electrode are occasionally referred to as a hole injecting layer and an electron injecting layer, respectively, and a hole injecting material and an electron injecting material are included in a hole transporting material and an electron transporting material, respectively in the following description.

The hole transporting layer is formed by a method of laminating or mixing one kind or two or more kinds of a hole transporting material, or a method of using a mixture of a hole transporting material and a polymeric binding agent. The hole transporting layer may be formed by adding an inorganic salt such as iron (III) chloride to a hole transporting material. The hole transporting material is not particularly limited if a compound which forms a thin film necessary for producing a light emitting device to be capable of injecting a hole from an anode and additionally transporting the hole. Preferable examples thereof include triphenylamine derivatives such as 4,4'-bis(N-(3-methylphenyl)-N-phenylamino)biphenyl, 4,4'-bis(N-(1-naphthyl)-N-phenylamino)biphenyl and 4,4',4''-tris(3-methylphenyl(phenyl)amino)triphenylamine, biscarbazole derivatives such as bis(N-allylcarbazole) or bis(N-alkylcarbazole), heterocyclic compounds such as a pyrazoline derivative, stilbene compound, hydrazone compound, benzofuran derivative, thiophene derivative, oxadiazole derivative, phthalocyanine derivative and porphyrin derivative, and polymers such as polycarbonate having the above-mentioned monomers as a side chain, styrene derivative having the above-mentioned monomers as a side chain, polythiophene, polyaniline, polyfluorene, polyvinyl carbazole and polysilane.

In the present invention, the luminescent layer may be either of a monolayer and a multilayer, either of which is formed from a luminescent material having a host material and a dopant material as a primary component. The luminescent material may be either of a mixture of a host material and a dopant material and a host material singly. That is, with regard to a light emitting device of the present invention, in each of the luminescent layers, only one of a host material and a dopant material may emit light, or both of a host material and a dopant material may emit light. Each of a host material and a dopant material may be of either one kind or a combination of plural kinds. A dopant material may be contained in a host material either all over or partially. A dopant material may be either laminated or dispersed. The amount of a dopant material is preferably used at 20% by weight or less, more preferably 10% by weight or less, with respect to a host material for the reason that too large amount thereof causes a concentration quenching phenomenon. With regard to a doping method, the formation can be performed by codeposition with a host material, and deposition may simultaneously be performed after previously mixing with a host material.

An anthracene compound represented by the general formula (1) or (3) is appropriately used as a luminescent material of a light emitting device of the present invention. A light emitting device material of the present invention is appropriately used as a blue luminescent material by reason of offering intense light emission in blue color region, and can also be used as a material for a green to red light emitting device and a white light emitting device. An anthracene compound of the present invention may be used as a dopant material and appropriately as a host material by reason of excellent thin film stability.

Ionization potential of an anthracene compound represented by the general formula (1) or (3) of the present invention is not particularly limited, being preferably 4.6 or higher to 6.0 eV or lower, more preferably 4.8 or higher to 5.8 eV or lower. The absolute value of ionization potential occasionally varies with a measuring method, and ionization potential of the present invention is a value by measuring a thin film deposited to a thickness of 30 to 100 nm on an ITO glass substrate with the use of an atmosphere type ultraviolet light electronic analysis instrument (AC-1, manufactured by RIKENKIKI CO., LTD.).

The host material used in the present invention need not be limited to only one kind of an anthracene compound represented by the general formula (1) or (3) of the present invention, and plural anthracene compounds of the present invention may be used therefor by mixture, or one or more kinds of other host materials may be used therefor by mixture with an anthracene compound of the present invention. Examples of mixable host materials to be appropriately used include fused ring derivatives as a luminophor such as anthracene and pyrene, an aromatic amine derivative such as N,N'-dinaphthyl-N,N'-diphenyl-4,4'-diphenyl-1,1'-diamine, a metal chelated oxynoid compound commencing with tris(8-quinolinate)aluminum (III), a bisstyryl derivative such as a distyrylbenzene derivative, a tetraphenyl butadiene derivative, indene derivative, coumarin derivative, oxadiazole derivative, pyrrolopyridine derivative, perynone derivative, cyclopentadiene derivative, oxadiazole derivative, carbazole derivative, pyrrolopyrrole derivative, and polymers such as a polyphenylene vinylene derivative, polyparaphenylene derivative, polyfluorene derivative, polyvinyl carbazole derivative and polythiophene derivative.

The dopant material contained in a luminescent material is not particularly limited, examples thereof including compounds having an aryl ring such as naphthalene, anthracene, phenanthrene, pyrene, triphenylene, perylene, fluorene and indene and derivatives thereof (such as 2-(benzothiazole-2-yl)-9,10-diphenylanthracene and 5,6,11,12-tetraphenylnaphthacene), compounds having a heteroaryl ring and derivatives thereof, such as furan, pyrrole, thiophene, silole, 9-silafluorene, 9,9'-spirobisilafluorene, benzothiophene, benzofuran, indole, dibehzothiophene, dibenzofuran, imidazopyridine, phenanthroline, pyrazine, naphthyridine, quinoxaline, pyrrolopyridine and thioxanthene, a distyrylbenzene derivative, aminostyryl derivatives such as, 4,4'-bis(2-(4-diphenylaminophenyl)ethenyl)biphenyl and 4,4'-bis(N-(stilbene-4-yl)-N-phenylamino)stilbene, an aromatic acetylene derivative, tetraphenyl butadiene derivative, stilbene derivative, aldazine derivative, pyrromethene derivative, diketopyrrolo[3,4-c]pyrrole derivative, a coumarin derivative such as 2,3,5,6-1H, 4H-tetrahydro-9-(2'-benzothiazolyl)quinolizino[9, 9a,1-gh] coumarin, azole derivatives and metal complexes thereof, such as imidazole, thiazole, thiadiazole, carbazole, oxazole, oxadiazole and triazole, and an aromatic amine derivative typified by N,N'-diphenyl-N,N'-di(3-methylphenyl)-4,4'-diphenyl-1,1'-diamine. Among these, it is preferable that the use of a fused aromatic ring derivative having an electron-accepting substituent as dopant brings more notable effect of thin film stability offered by an anthracene compound of the present invention. Specifically, particularly preferable examples of dopant include a pyrene compound having a benzazol group typified by 1-(benzoxazole-2-yl)-3,8-bis(4-methylphenyl)pyrene.

In the present invention, the electron transporting layer is a layer such that an electron is injected from a cathode and further transported. It is desired that the electron transporting layer has high electron injection efficiency and efficiently transports the injected electron. Thus, it is desirable that the electron transporting layer is composed of a material such that electron affinity is high, electron mobility is high, stability is excellent, and impurities as trap are caused with difficulty during production and use. However, in consideration of transportation balance between a hole and an electron, if the electron transporting layer mainly plays a role in being capable of efficiently blocking a hole from an anode from flowing to the side of a cathode without recombining, the effect of improving luminous efficiency becomes equal as in the case of being composed of a material with high electron transporting ability even though composed of a material with not so high electron transporting ability. Accordingly, a hole blocking layer capable of efficiently preventing a hole from moving is also included as the same meaning in the electron transporting layer in the present invention.

The electron transporting material used for the electron transporting layer is not particularly limited, examples thereof including compounds having a fused aryl ring and derivatives thereof, such as naphthalene and anthracene, a styryl aromatic ring derivative typified by 4,4'-bis(diphenylethenyl)biphenyl, a perylene derivative, perynone derivative, coumarin derivative, naphthalimide derivative, quinone derivatives such as anthraquinone and diphenoquinone, a phosphine oxide derivative, carbazole derivative, indole derivative, a quinolinol complex such as tris(8-quinolinolate) aluminum (III), a hydroxyazole complex such as a hydroxyphenyloxazole complex, an azomethine complex, tropolone metal complex, flavonol metal complex, and a compound having a heteroaryl ring with electron-accepting nitrogen.

The electron-accepting nitrogen in the present invention signifies a nitrogen atom forming a multiple bond with a neighboring atom. A nitrogen atom has high electronegativity, so that the multiple bond has electron-accepting properties. Therefore, a heteroaryl ring containing electron-accepting nitrogen has high electron affinity. Examples of a heteroaryl ring containing electron-accepting nitrogen include a pyridine ring, pyrazine ring, pyrimidine ring, quinoline ring, quinoxaline ring, naphthyridine ring, pyrimidopyrimidine ring, benzoquinoline ring, phenanthroline ring, imidazole ring, oxazole ring, oxadiazole ring, triazole ring, thiazole ring, thiadiazole ring, benzoxazole ring, benzothiazole ring, benzimidazole ring and phenanthroimidazole ring.

A compound having a heteroaryl ring structure containing electron-accepting nitrogen of the present invention is preferably composed of an element selected from among carbon, hydrogen, nitrogen, oxygen, silicon and phosphorus. A compound having a heteroaryl ring structure containing electron-accepting nitrogen, which is composed of these elements, has so high electron transporting ability as to be capable of significantly reducing driving voltage.

Preferable examples of a compound having a heteroaryl ring structure containing electron-accepting nitrogen, composed of an element selected from among carbon, hydrogen, nitrogen, oxygen, silicon and phosphorus, include a benzimidazole derivative, benzoxazole derivative, benzothiazole derivative, oxadiazole derivative, thiadiazole derivative, triazole derivative, pyrazine derivative, phenanthroline derivative, quinoxaline derivative, quinoline derivative, benzoquinoline derivative, oligopyridine derivatives such as bipyridine and terpyridine, quinoxaline derivative, and naphthyridine derivative. Among these, the following are preferably used in view of electron transporting ability: an imidazole derivative such as tris(N-phenylbenzimidazole-2-yl) benzene, oxadiazole derivative such as 1,3-bis[(4-tert-butylphenyl)1,3,4-oxadiazolyl]phenylene, triazole derivative such as N-naphtyl-2,5-diphenyl-1,3,4-triazole, phenanthroline derivatives such as bathocuproine and 1,3-bis(1,10-phenanthroline-9-yl)benzene, benzoquinoline derivative such as 2,2'-bis(benzo[h]quinoline-2-yl)-9,9'-spirobifluorene, bipyridine derivative such as 2,5-bis(6'-(2',2''-bipyridyl))-1,1-dimethyl-3,4-diphenylsilole, terpyridine derivative such as 1,3-bis(4'-(2,2':6'2''-terpyridinyl))benzene, and naphthyridine derivative such as bis(1-naphtyl)-4-(1,8-naphthyridine-2-yl)phenylphosphine oxide. In addition, phenanthroline dimers such as 1,3-bis(1,10-phenanthroline-9-yl) benzene, 2,7-bis(1,10-phenanthroline-9-yl)naphthalene and 1,3-bis(2-phenyl-1,10-phenanthroline-9-yl)benzene, and a bipyridine dimer such as 2,5-bis(6'-(2',2''-bipyridyl))-1,1-dimethyl-3,4-diphenylsilole have so significantly high effect of improving durability when combined with an anthracene compound represented by the general formula (1) or (3) of the present invention, as to be included in particularly preferable examples.

The above-mentioned electron transporting material is used singly, and two or more kinds of the above-mentioned electron transporting materials may be used by mixture, or one or more kinds of other electron transporting materials may be used by mixture with the above-mentioned electron transporting materials. Metals such as alkaline metal and alkaline earth metal can also be used by mixture therewith. Ionization potential of the electron transporting layer is not particularly limited, being preferably 5.8 or higher to 8.0 eV or lower, more preferably 6.0 or higher to 7.5 eV or lower.

A method of forming each of the above-mentioned layers composing a light emitting device is not particularly limited, such as resistance heating deposition, electron beam deposition, sputtering, molecular stacking method and coating method; typically, resistance heating deposition or electron beam deposition is preferable in view of device performance.

The thickness of the layers cannot be limited by reason of depending on resistance values of luminescent substances, and yet is selected from 1 to 1000 nm. The film thickness of each of the luminescent layer, the electron transporting layer and the hole transporting layer is preferably 1 or more to 200 nm or less, more preferably 5 or more to 100 nm or less.

A light emitting device of the present invention has the function of being capable of converting electric energy into light. Wherein, direct current is mainly used as electric energy, and pulsed current and alternating current can also be used. Current values and voltage values are not particularly limited, and yet should be selected so that as low energy as possible allows the highest brightness in consideration of power consumption and lifetime of the device.

A light emitting device of the present invention is appropriately used, for example, as a display for displaying in matrix and/or segment system.

A matrix system is such that pixels for displaying are two-dimensionally disposed in lattice, mosaic or the like to display characters and images by an assembly of the pixels. Shapes and sizes of the pixels are determined by use thereof. For example, quadrangular pixels of 300 µm or less on a side are typically used for displaying images and characters of a personal computer, monitor and television, and pixels in the order of mm on a side are used in the case of a large-size display such as a display panel. Pixels in the same color are merely arrayed in the case of monochrome display, while pixels in red, green and blue are arrayed for displaying in the case of color display. In this case, a delta type and a stripe type are typically offered. A drive system of this matrix may be either of line-sequential drive system and active matrix. Line-sequential drive is simple in structure thereof; however, active matrix is occasionally more excellent in consideration of operating characteristics, so that these need to be properly used according to the use.

A segment system in the present invention is such that a pattern is formed so as to display previously determined information and disposition of this pattern allows a determined area to emit light. Examples thereof include time and temperature display in a digital clock and thermometer, operation display of an audio apparatus and electromagnetic cooker, and panel display of an automobile. The above-mentioned matrix display and segment display may coexist in the same panel.

A light emitting device of the present invention is preferably used as a backlight of various apparatuses. A backlight is mainly used for the purpose of improving visibility of a display device which does not emit light for itself; a liquid crystal display device, clock, audio device, automobile panel, display board and mark. In particular, a light emitting device of the present invention is preferably used for a backlight of a liquid crystal display device, among these, a personal computer about which production of the thinner type has been studied, whereby a backlight of a thinner and lighter-weight type than the conventional one can be provided.

EXAMPLES

Hereinafter, the present invention is explained with reference to examples but is not limited thereto. The number of a compound in each of the following examples denotes the number of a compound described in the above-mentioned chemical formulae. An evaluation method on structural analysis is described below.

$^1$H-NMR was measured in chloroform-d solution by using superconductive FTNMR EX-270 (manufactured by JEOL Ltd.).

Example 1

A Synthetic Method of a Compound [3]

A mixed solution of 1 g of 2-tert-butyl-9,10-dibromoanthracene, 1.5 g of 4-dibenzofuranboronic acid, 2.2 g of tripotassium phosphate, 0.33 g of tetrabutylammonium bromide, 5 mg of palladium acetate and 40 ml of dimethylformamide was heated while stirred under nitrogen gas stream at a temperature of 130° C. for 6 hours. After cooling the mixed solution to room temperature, 50 ml of water was injected thereto to extract 100 ml of dichloromethane therefrom. The organic layer was washed twice in 50 ml of water, dried by magnesium sulfate and thereafter concentrated by evaporation. The organic layer was purified by silica gel column chromatography and vacuum dried to obtain 0.6 g of a white crystal. The results of $^1$H-NMR analysis of the obtained powder are as follows.

$^1$H-NMR (CDCl$_3$ (d=ppm)): 1.16 (s, 9H), 7.26-7.30 (m, 2H), 7.34-7.44 (m, 7H), 7.57-7.68 (m, 8H), 8.09 (m, 2H), 8.18 (m, 2H)

This compound [3] was purified by sublimation under a pressure of $1\times10^{-3}$ Pa at a temperature of approximately 260° C. by using an oil diffusion pump, and thereafter used as a light emitting device material. HPLC purity (area % at a measuring wavelength of 254 nm) was 98.6% before purification by sublimation and 99.0% after purification by sublimation.

Example 2

Synthesis of a Compound [58]

A solution of 8.5 g of carbazole, 50 g of 1,4-diiodobenzene, 3.9 g of copper powder, 8.43 g of potassium carbonate and 8.66 g of sodium sulfate in 500 ml of nitrobenzene as a solvent was heated while stirred under nitrogen atmosphere at a temperature of 200° C. for 2 days. Thereafter, most of nitrobenzene was distilled out under reduced pressure to thereafter add 400 ml of dichloromethane thereto. The solid was filtered off, thereafter concentrated by evaporation and washed in hexane. The solid was purified by silica gel column chromatography and vacuum dried to thereafter obtain 9.16 g of 1-(4-iodophenyl)carbazole.

A solution of 12 g of 9-bromoanthracene, 10 g of 4-tert-butylphenylboronic acid, 19.9 g of tripotassium phosphate, 3.02 g of tetrabutylammonium bromide and 106 mg of palladium acetate in 300 ml of dimethylformamide as a solvent was heated while stirred under nitrogen atmosphere at a temperature of 130° C. for 5 hours. After cooling the solution to room temperature, 400 ml of water was injected thereto and filtered. The solid separated by filtration was purified by silica gel column chromatography and vacuum dried to thereafter obtain 13.3 g of 9-(4'-tert-butylphenyl)anthracene.

A mixed solution of 13.3 g of the above-mentioned 9-(4-tert-butylphenyl)anthracene, 7.52 g of bromine and 300 ml of carbon tetrachloride was heated to reflux under nitrogen atmosphere for 1 hour. After cooling the mixed solution to room temperature, 200 ml of water was injected thereto to extract 200 ml of dichloromethane therefrom. The organic layer was washed twice in 200 ml of water, dried by magnesium sulfate and thereafter concentrated by evaporation. The organic layer was washed twice in 100 ml of hexane and vacuum dried to thereafter obtain 16.09 g of 9-bromo-10-(4-tert-butylphenyl)anthracene.

15.4 g of the above-mentioned 9-bromo-10-(4-tert-butylphenyl) anthracene was dissolved in 380 ml of tetrahydrofuran to drop 30 ml of n-butyllithium (1.6 M-hexane solution) thereto under nitrogen atmosphere at a temperature of 0° C. The solution was stirred at a temperature of 0° C. for 30 minutes and thereafter cooled to a temperature of –80° C. to drop 18.2 ml of triisopropyl borate thereto. The solution was heated up to room temperature by standing at room temperature and thereafter stirred at room temperature for 3 hours. 400 ml of 10%-hydrochloric acid was dropped thereto and further stirred at room temperature for 2 hours to thereafter extract 300 ml of diethyl ether therefrom. The organic layer was washed in 100 ml of 5%-sodium carbonate aqueous solution, washed in 100 ml of water, then dried by magnesium sulfate and thereafter concentrated by evaporation. The organic layer was purified by silica gel column chromatography (developing solvent was in the order of dichloromethane/hexane=1/1, dichloromethane and dichloromethane/methanol=50/1) and vacuum dried to thereafter obtain 6.78 g of 9-(4-tert-butylphenyl)-10-anthraceneboronic acid.

A mixed solution of 2.1 g of the above-mentioned 1-(4-iodophenyl)carbazole, 2 g of 9-(4-tert-butylphenyl)-10-anthraceneboronic acid, 2.4 g of tripotassium phosphate, 364 mg of tetrabutylammonium bromide, 25 mg of palladium acetate and 50 ml of dimethylformamide was heated while stirred under nitrogen atmosphere at a temperature of 130° C. for 4 hours. After cooling the mixed solution to room temperature, 400 ml of water was injected thereto and filtered. The solid separated by filtration was purified by silica gel column chromatography (dichloromethane/methanol=1/3) and vacuum dried to thereafter obtain 1.81 g of a compound [58]. The results of $^1$H-NMR analysis of the obtained powder are as follows.

$^1$H-NMR (CDCl$_3$ (d=ppm)): 1.50 (s, 9H), 7.33-7.54 (m, 10H), 7.62-7.85 (m, 12H), 8.21 (d, 2H)

This compound [58] was purified by sublimation under a pressure of 1×10$^{-3}$ Pa at a temperature of approximately 260° C. by using an oil diffusion pump, and thereafter used as a light emitting device material. HPLC purity (area % at a measuring wavelength of 254 nm) was 99.5% before purification by sublimation and 99.8% after purification by sublimation.

Example 3

Synthesis of a Compound [84]

140 mg of a compound [84] was obtained in the same manner as Example 2 except for replacing 1-(4-iodophenyl)carbazole with 1-(6-trifluoromethanesulfonyloxynaphthalene-2-yl)carbazole. $^1$H-NMR was not measured by reason of being hardly soluble in commercial heavy hydrogen solvent. This compound [84] was purified by sublimation under a pressure of 1×10$^{-3}$ Pa at a temperature of approximately 280° C. by using an oil diffusion pump, and thereafter used as a light emitting device material. HPLC purity (area % at a measuring wavelength of 254 nm) was 99.5% before purification by sublimation and 99.9% after purification by sublimation.

Example 4

Synthesis of a Compound [103]

2.23 g of a compound [103] was obtained in the same manner as Example 2 except for replacing 1-(4-iodophenyl)carbazole with 1-(3-iodophenyl)carbazole. The results of $^1$H-NMR analysis of the obtained powder are as follows.

$^1$H-NMR (CDCl$_3$ (d=ppm)): 1.48 (s, 9H), 7.29-7.88 (m, 22H), 8.14 (d, 2H)

This compound [103] was purified by sublimation under a pressure of 1.0×10$^{-3}$ Pa at a temperature of approximately 260° C. by using an oil diffusion pump, and thereafter used as a light emitting device material. HPLC purity (area % at a measuring wavelength of 254 nm) was 99.5% before purification by sublimation and 99.8% after purification by sublimation.

Example 5

A Synthetic Method of a Compound [122]

A mixed solution of 18.4 g of ortho-cyanobenzyl bromide, 25 g of 4-tert-butylphenylboronic acid, 40 g of tripotassium phosphate, 490 mg of triphenylphosphine, 210 mg of palladium acetate and 280 ml of toluene was heated while stirred under nitrogen gas stream at a temperature of 80° C. for 4 hours. After cooling the mixed solution to room temperature, 50 ml of water was injected thereto to extract 100 ml of toluene therefrom. The organic layer was washed twice in 50 ml of water, dried by magnesium sulfate and thereafter concentrated by evaporation. The organic layer was purified by silica gel column chromatography and vacuum dried to thereafter obtain 2-(4-tert-butylbenzyl)benzonitrile.

A mixed solution of 6.7 g of the above-mentioned 2-(4-tert-butylbenzyl)benzonitrile, 70 ml of commercial 1 mol/l-4-chlorophenyl magnesium bromide solution and 15 ml of toluene was heated to reflux under nitrogen gas stream for 1 hour. After cooling the mixed solution to room temperature, 25 ml of saturated ammonium chloride aqueous solution was slowly added thereto. 50 ml of water was injected thereto to extract 100 ml of dichloromethane. The organic layer was washed twice in 50 ml of water, dried by magnesium sulfate and thereafter concentrated by evaporation. After vacuum drying this compound, a mixed solution of 20 ml of 25%-sulfuric acid aqueous solution and 20 ml of toluene was heated to reflux thereto under nitrogen gas stream for 6 hours. After cooling the compound to room temperature, 50 ml of water was injected thereto to extract 100 ml of dichloromethane therefrom. The organic layer was washed twice in 50 ml of water, dried by magnesium sulfate and thereafter concentrated by evaporation. The organic layer was purified by silica gel column chromatography and vacuum dried to thereafter obtain [2-(4-tert-butylbenzyl)phenyl](4-chlorophenyl)methanone.

A mixed solution of 6.9 g of the above-mentioned [2-(4-tert-butylbenzyl)phenyl](4-chlorophenyl)methanone, 100 ml of hydrobromic acid and 200 ml of acetic acid was heated to reflux under nitrogen gas stream for 7 hours. After cooling the mixed solution to room temperature, 50 ml of water was injected thereto to extract 100 ml of dichloromethane therefrom. The organic layer was washed twice in 50 ml of water, dried by magnesium sulfate and thereafter concentrated by evaporation. The organic layer was purified by silica gel column chromatography and vacuum dried to thereafter obtain 2-tert-butyl-9-(4-chlorophenyl)anthracene.

A mixed solution of 6 g of the above-mentioned 2-tert-butyl-9-(4-chlorophenyl)anthracene, 3.5 g of N-bromosuccinimide and 55 g of dimethylformamide was stirred under nitrogen gas stream at room temperature for 3 hours. 50 ml of water was injected thereto to extract 100 ml of dichloromethane therefrom. The organic layer was washed twice in 50 ml of water, dried by magnesium sulfate and thereafter concentrated by evaporation. The organic layer was purified by silica gel column chromatography to obtain 10-bromo-2-tert-butyl-9-(4-chlorophenyl)anthracene.

A mixed solution of 1.95 g of the above-mentioned 10-bromo-2-tert-butyl-9-(4-chlorophenyl)anthracene, 622 mg of phenylboronic acid, 1.95 g of tripotassium phosphate, 300 mg of tetrabutyl ammonium bromide, 20 mg of palladium acetate and 50 ml of dimethylformamide was heated while stirred under nitrogen gas stream at a temperature of 130° C. for 5 hours. After cooling the mixed solution to room temperature, 100 ml of water was injected thereto and filtered. The solid separated by filtration was purified by silica gel column chromatography and vacuum dried to thereafter obtain 2-tert-butyl-9-(4-chlorophenyl)-10-phenylanthracene.

A mixed solution of 1.6 g of the above-mentioned 2-tert-butyl-9-(4-chlorophenyl)-10-phenylanthracene, 953 mg of carbazole, 548 mg of sodium tert-butoxide, 99 mg of tri-tert-butylphosphine tetrafluoroborate, 220 mg of bis(dibenzylideneacetone)palladium and 35 ml of deaerated ortho-xylene was heated while stirred under nitrogen gas stream at a temperature of 140° C. for 1 hour. After cooling the mixed solution to room temperature, 25 ml of water was injected thereto to extract 50 ml of dichloromethane therefrom. The organic layer was washed twice in 25 ml of water, dried by magnesium sulfate and thereafter concentrated by evaporation. The organic layer was purified by silica gel column chromatography and vacuum dried to thereafter obtain a compound [122]. The results of $^1$H-NMR analysis of the obtained powder are as follows.

$^1$H-NMR (CDCl$_3$ (d=ppm)): 1.33 (s, 9H), 2.56 (s, 3H), 7.33-7.88 (m, 21H), 8.22 (d, 2H)

This compound [122] was purified by sublimation under a pressure of 1×10$^{-3}$ Pa at a temperature of approximately 260° C. by using an oil diffusion pump, and thereafter used as a light emitting device material. HPLC purity (area % at a measuring wavelength of 254 nm) was 99.4% before purification by sublimation and 99.6% after purification by sublimation.

Example 6

A Synthetic Method of a Compound [126]

A mixed solution of 18.4 g of ortho-cyanobenzyl bromide, 25 g of 4-tert-butylphenylboronic acid, 40 g of tripotassium phosphate, 490 mg of triphenylphosphine, 210 mg of palladium acetate and 280 ml of toluene was heated while stirred under nitrogen gas stream at a temperature of 80° C. for 4 hours. After cooling the mixed solution to room temperature, 50 ml of water was injected thereto to extract 100 ml of toluene therefrom. The organic layer was washed twice in 50 ml of water, dried by magnesium sulfate and thereafter concentrated by evaporation. The organic layer was purified by silica gel column chromatography and vacuum dried to thereafter obtain 2-(4-tert-butylbenzyl)benzonitrile.

A mixed solution of 7 g of the above-mentioned 2-(4-tert-butylbenzyl)benzonitrile, 36.5 ml of adjusted 2 mol/l-2-naphtyl magnesium bromide solution and 16 ml of toluene was heated to reflux under nitrogen gas stream for 3 hours. After cooling the mixed solution to room temperature, 25 ml of saturated ammonium chloride aqueous solution was slowly added thereto. 50 ml of water was injected thereto to extract 50 ml of toluene therefrom. The organic layer was washed twice in 50 ml of water, dried by magnesium sulfate and thereafter concentrated by evaporation. After vacuum drying this compound, a mixed solution of 25 ml of 25%-sulfuric acid aqueous solution and 25 ml of toluene was heated to reflux thereto under nitrogen gas stream for 5 hours. After cooling the compound to room temperature, 50 ml of water was injected thereto to extract 50 ml of toluene therefrom. The organic layer was washed twice in 50 ml of water, dried by magnesium sulfate and thereafter concentrated by evaporation. The organic layer was purified by silica gel column chromatography and vacuum dried to thereafter obtain [2-(4-tert-butylbenzyl)phenyl](naphthalene-2-yl)methanone.

A mixed solution of 6.1 g of the above-mentioned [2-(4-tert-butylbenzyl)phenyl](naphthalene-2-yl)methanone, 80 ml of hydrobromic acid and 160 ml of acetic acid was heated to reflux under nitrogen gas stream for 11 hours. After cooling the mixed solution to room temperature, 50 ml of water was injected thereto to extract 100 ml of dichloromethane therefrom. The organic layer was washed twice in 50 ml of water, dried by magnesium sulfate and thereafter concentrated by evaporation. The organic layer was purified by silica gel column chromatography and vacuum dried to thereafter obtain 2-tert-butyl-9-(naphthalene-2-yl)anthracene.

A mixed solution of 2.2 g of the above-mentioned 2-tert-butyl-9-(naphthalene-2-yl)anthracene, 3.7 g of N-bromosuccinimide and 30 ml of dimethylformamide was stirred under nitrogen gas stream at room temperature for 1 hour. 50 ml of water was injected thereto to extract 100 ml of dichloromethane therefrom. The organic layer was washed twice in 50 ml of water, dried by magnesium sulfate and thereafter concentrated by evaporation. The organic layer was purified by silica gel column chromatography to obtain 10-bromo-2-tert-butyl-9-(naphthalene-2-yl)anthracene.

A mixed solution of 700 mg of the above-mentioned 10-bromo-2-tert-butyl-9-(naphthalene-2-yl)anthracene, 740 mg of 9-[4-(4,4,5,5-tetramethyl-[1,3,2]dioxaborolane-2-yl)phenyl]carbazole, 680 mg of tripotassium phosphate, 100 mg of tetrabutyl ammonium bromide, 7 mg of palladium acetate and 16 mg of dimethylformamide was heated while stirred under nitrogen gas stream at a temperature of 130° C. for 4 hours. After cooling the mixed solution to room temperature, 50 ml of water was injected thereto and filtered. The solid separated by filtration was purified by silica gel column chromatography and vacuum dried to thereafter obtain a compound [126]. The results of $^1$H-NMR analysis of the obtained powder are as follows.

$^1$H-NMR (CDCl$_3$ (d=ppm)): 1.25 (s, 9H), 7.31-8.22 (m, 24H), 8.21 (d, 2H)

This compound [126] was purified by sublimation under a pressure of 1×10$^{-3}$ Pa at a temperature of approximately 260° C. by using an oil diffusion pump, and thereafter used as a light emitting device material. HPLC purity (area % at a measuring wavelength of 254 nm) was 99.1% before purification by sublimation and 99.3% after sublimation.

Example 7

A Synthetic Method of a Compound [130]

A mixed solution of 18.4 g of ortho-cyanobenzyl bromide, 25 g of 4-tert-butylphenylboronic acid, 40 g of tripotassium phosphate, 490 mg of triphenylphosphine, 210 mg of palladium acetate and 280 ml of toluene was heated while stirred under nitrogen gas stream at a temperature of 80° C. for 4 hours. After cooling the mixed solution to room temperature, 50 ml of water was injected thereto to extract 100 ml of toluene therefrom. The organic layer was washed twice in 50 ml of water, dried by magnesium sulfate and thereafter concentrated by evaporation. The organic layer was purified by silica gel column chromatography and vacuum dried to thereafter obtain 2-(4-tert-butylbenzyl)benzonitrile.

A mixed solution of 7 g of the above-mentioned 2-(4-tert-butylbenzyl)benzonitrile, 36.5 ml of adjusted 2 mol/l-phenyl magnesium bromide solution and 16 ml of toluene was heated to reflux under nitrogen gas stream for 2 hours. After cooling the mixed solution to room temperature, 25 ml of saturated ammonium chloride aqueous solution was slowly added thereto. 50 ml of water was injected thereto to extract 50 ml of toluene therefrom. The organic layer was washed twice in 50 ml of water, dried by magnesium sulfate and thereafter concentrated by evaporation. After further vacuum drying this compound, a mixed solution of 25 ml of 25%-sulfuric acid aqueous solution and 25 ml of toluene was heated to reflux thereto under nitrogen gas stream for 5 hours. After cooling the compound to room temperature, 50 ml of water was injected thereto to extract 50 ml of toluene therefrom. The organic layer was washed twice in 50 ml of water, dried by magnesium sulfate and thereafter concentrated by evaporation. The organic layer was purified by silica gel column chromatography and vacuum dried to thereafter obtain 2-(4-tert-butylbenzyl)benzophenone.

A mixed solution of 8.7 g of the above-mentioned 2-(4-tert-butylbenzyl)benzophenone, 130 ml of hydrobromic acid and 260 ml of acetic acid was heated to reflux under nitrogen gas stream for 8 hours. After cooling the mixed solution to room temperature, 50 ml of water was injected thereto to extract 100 ml of dichloromethane therefrom. The organic layer was washed twice in 50 ml of water, dried by magnesium sulfate and thereafter concentrated by evaporation. The organic layer was purified by silica gel column chromatography and vacuum dried to thereafter obtain 2-tert-butyl-9-phenylanthracene.

A mixed solution of 6.8 g of the above-mentioned 2-tert-butyl-9-phenylanthracene, 4.3 g of N-bromosuccinimide and 60 ml of dimethylformamide was stirred under nitrogen gas stream at room temperature for 2 hours. 50 ml of water was injected thereto to extract 100 ml of dichloromethane therefrom. The organic layer was washed twice in 50 ml of water, dried by magnesium sulfate and thereafter concentrated by evaporation. The organic layer was purified by silica gel column chromatography to obtain 10-bromo-2-tert-butyl-9-phenylanthracene.

A mixed solution of 2.2 g of the above-mentioned 10-bromo-2-tert-butyl-9-phenylanthracene, 2.2 g of 9-[3-(4,4,5,5-tetramethyl-[1,3,2]dioxaborolane-2-yl)phenyl]carbazole, 2.4 g of tripotassium phosphate, 360 mg of tetrabutyl ammonium bromide, 25 mg of palladium acetate and 60 ml of dimethylformamide was heated while stirred under nitrogen gas stream at a temperature of 130° C. for 5 hours. After cooling the mixed solution to room temperature, 100 ml of water was injected thereto and filtered. The solid separated by filtration was purified by silica gel column chromatography and vacuum dried to thereafter obtain a compound [130]. The results of $^1$H-NMR analysis of the obtained powder are as follows.

$^1$H-NMR (CDCl$_3$ (d=ppm)): 1.26 (s, 9H), 7.23-7.86 (m, 22H), 8.11 (d, 2H)

This compound [130] was purified by sublimation under a pressure of $1\times10^{-3}$ Pa at a temperature of approximately 260° C. by using an oil diffusion pump, and thereafter used as a light emitting device material. HPLC purity (area % at a measuring wavelength of 254 nm) was 99.4% before purification by sublimation and 99.6% after purification by sublimation.

Example 8

A Synthetic Method of a Compound [132]

A compound [132] was obtained in the same manner as Example 6 except for replacing 9-[4-(4,4,5,5-tetramethyl-[1,3,2]dioxaborolane-2-yl)phenyl]carbazole with 9-[3-(4,4,5,5-tetramethyl-[1,3,2]dioxaborolane-2-yl)phenyl]carbazole. The results of $^1$H-NMR analysis of the obtained powder are as follows.

$^1$H-NMR (CDCl$_3$ (d=ppm)): 1.23 (s, 9H), 7.27-8.10 (m, 24H), 8.15 (d, 2H)

This compound [132] was purified by sublimation under a pressure of $1\times10^{-3}$ Pa at a temperature of approximately 260° C. by using an oil diffusion pump, and thereafter used as a light emitting device material. HPLC purity (area % at a measuring wavelength of 254 nm) was 99.5% before purification by sublimation and 99.6% after purification by sublimation.

Example 9

A glass substrate (manufactured by ASAHI GLASS CO., LTD., 15 Ω/square, electron beam deposition product) on which an ITO transparent conductive film was accumulated with a thickness of 150 nm was cut to a size of 30×40 mm, which ITO conductive film was patterned by a photolithographic method to produce a light emitting part and an electrode extraction part. The obtained substrate was subject to ultrasonic cleaning with acetone and "SEMICOCLEAN (registered trademark) 56" (manufactured by Furuchi Chemical Corporation) for 15 minutes, and then cleaned with ultrapure water. Subsequently, the substrate was subject to ultrasonic cleaning with isopropyl alcohol for 15 minutes, and then immersed in hot methanol for 15 minutes and dried. Immediately before producing a device, this substrate was subject to UV-ozone treatment for 1 hour and further placed in a vacuum evaporator to exhaust until degree of vacuum in the evaporator became $5\times10^{-5}$ Pa or less. First, through a resistance heating method, copper phthalocyanine was deposited with a thickness of 10 nm as a hole injecting material and 4,4'-bis(N-(1-naphthyl)-N-phenylamino)biphenyl was deposited with a thickness of 50 nm as a hole transporting material. Next, with regard to a luminescent material, the compound [3] was deposited as a host material and D-1 represented by the following formula was deposited as a dopant material with a thickness of 35 nm so that doping concentration became 5%. Next, E-1 represented by the following formula was laminated with a thickness of 20 nm as an electron transporting material. Lithium was deposited with a thickness of 0.5 nm on the organic layer formed above to thereafter deposit aluminum with a thickness of 1000 nm as a cathode and produce a device of 5×5 mm square. The film thickness herein was an indicated value of a crystal oscillation film thickness monitor. When this light emitting device was subject to a direct current drive of 10 mA/cm$^2$, blue light emission with a high luminous efficiency of 3.8 lm/W was obtained. When this light emitting device was subject to continuous drive with a direct current of 10 mA/cm$^2$, brightness half-life period was 3000 hours.

(D-1)

[Chemical formula 22]

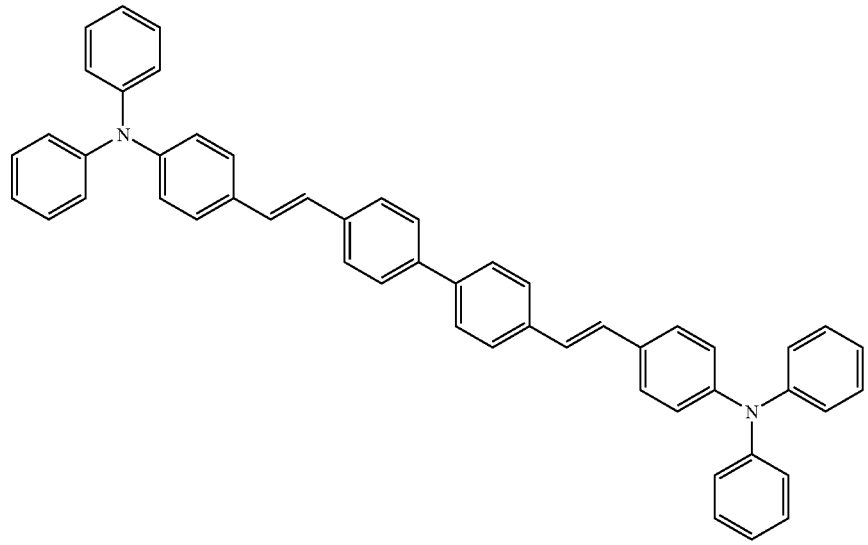

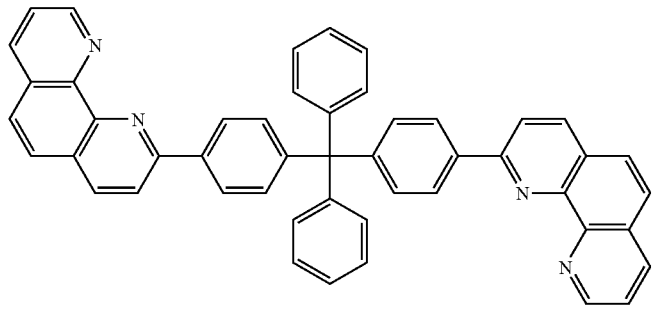 (E-1)

Examples 10 to 26

A light emitting device was produced in the same manner as Example 9 except for using materials described in Table 1 as host materials. The results of each example were shown in Table 1.

TABLE 1

| | Light Emission Layer | | Electron Transporting Layer | Color of Light Emission | Luminous Efficiency (lm/W) | Brightness half-life period (h) |
|---|---|---|---|---|---|---|
| | Host Material | Dopant Material | | | | |
| Example9 | Compound[3] | D-1 | E-1 | Blue | 3.8 | 3000 |
| Example10 | Compound[10] | D-1 | E-1 | Blue | 3.6 | 3700 |
| Example11 | Compound[14] | D-1 | E-1 | Blue | 3.5 | 2500 |
| Example12 | Compound[16] | D-1 | E-1 | Blue | 3.6 | 3400 |
| Example13 | Compound[25] | D-1 | E-1 | Blue | 2.5 | 2500 |
| Example14 | Compound[36] | D-1 | E-1 | Blue | 3.1 | 2800 |
| Example15 | Compound[37] | D-1 | E-1 | Blue | 4 | 2500 |
| Example16 | Compound[58] | D-1 | E-1 | Blue | 3.6 | 5500 |
| Example17 | Compound[84] | D-1 | E-1 | Blue | 3.5 | 4700 |
| Example18 | Compound[103] | D-1 | E-1 | Blue | 3.6 | 2700 |
| Example19 | Compound[122] | D-1 | E-1 | Blue | 4.1 | 5200 |
| Example20 | Compound[126] | D-1 | E-1 | Blue | 4.3 | 5000 |
| Example21 | Compound[130] | D-1 | E-1 | Blue | 4 | 5400 |
| Example22 | Compound[132] | D-1 | E-1 | Blue | 4.5 | 4800 |
| Example23 | Compound[80] | D-1 | E-1 | Blue | 3.5 | 2000 |
| Example24 | Compound[62] | D-1 | E-1 | Blue | 3.8 | 2100 |
| Example25 | Compound[113] | D-1 | E-1 | Blue | 3.2 | 2000 |
| Example26 | Compound[141] | D-1 | E-1 | Blue | 4.3 | 3500 |
| Comparative Example1 | H-1 | D-1 | E-1 | Blue | 2.8 | 200 |
| Comparative Example2 | H-2 | D-1 | E-1 | Blue | 3.1 | 50 |
| Comparative Example3 | H-3 | D-1 | E-1 | Blue | 2.8 | 800 |
| Comparative Example4 | H-4 | D-1 | E-1 | Blue | 2.9 | 300 |
| Comparative Example5 | H-5 | D-1 | E-1 | Blue | 2.7 | 600 |
| Comparative Example6 | H-6 | D-1 | E-1 | Blue | 2.4 | 400 |
| Comparative Example7 | H-7 | D-1 | E-1 | Blue | 2.6 | 700 |
| Comparative Example8 | H-8 | D-1 | E-1 | Blue | 2.5 | 800 |
| Comparative Example9 | H-9 | D-1 | E-1 | Blue | 2.7 | 500 |

Comparative Example 1

A light emitting device was produced in the same manner as Example 9 except for using H-1 represented by the following formula as a host material. When this light emitting device was subject to a direct current drive of 10 mA/cm$^2$, blue light emission with a luminous efficiency of 2.8 l m/W was obtained. When this light emitting device was subject to continuous drive with a direct current of 10 mA/cm$^2$, brightness half-life period was 200 hours.

[Chemical formula 23]

(H-1)
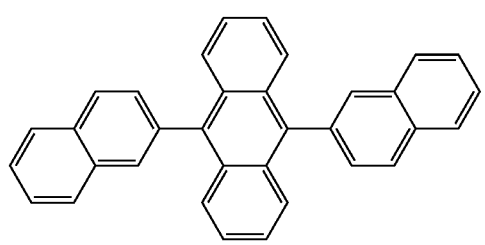

Comparative Examples 2 to 9

A light emitting device was produced in the same manner as Example 9 except for using materials described in Table 1 as host materials. The results of each comparative example were shown in Table 1. H-2, H-3, H-4, H-5, H-6, H-7, H-8 and H-9 in Table 1 were compounds represented by the following formulae.

[Chemical formula 24]

(H-2)
(H-3)
(H-4)
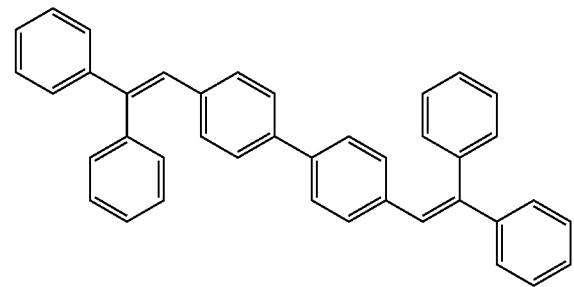
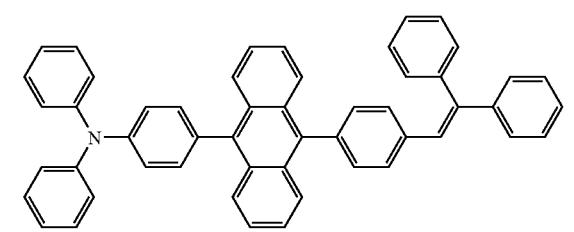

(H-5)
(H-6)
(H-7)
(H-8)
(H-9)
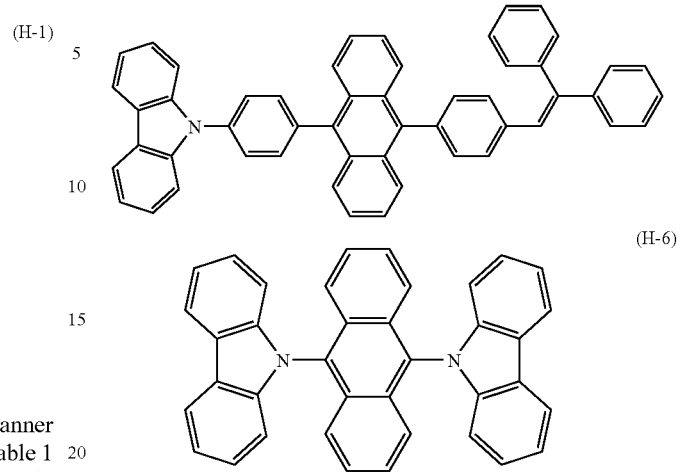
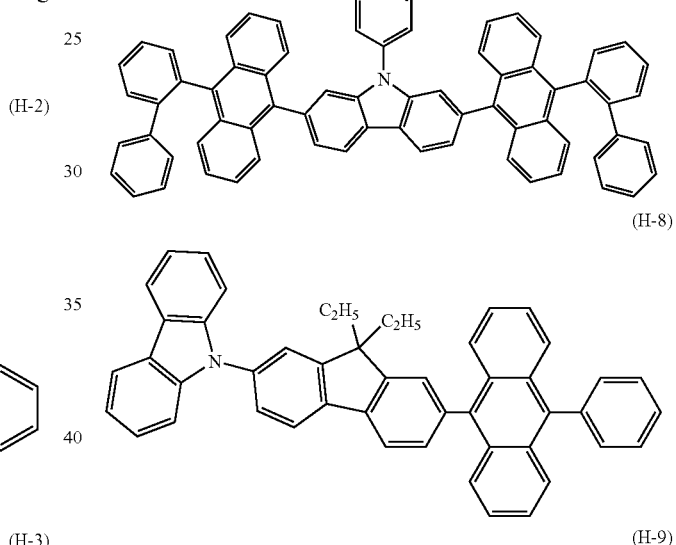
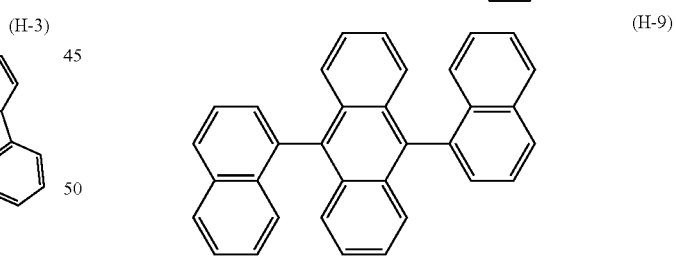
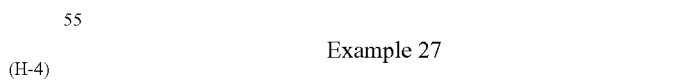

Example 27

A light emitting device was produced in the same manner as Example 9 except for using D-2 represented by the following formula as a dopant material so that doping concentration became 2%. When this light emitting device was subject to a direct current drive of 10 mA/cm$^2$, blue light emission with a high luminous efficiency of 2.6 l m/W was obtained. When this light emitting device was subject to continuous drive with a direct current of 10 mA/cm$^2$, brightness half-life period was 2800 hours.

[Chemical formula 25]

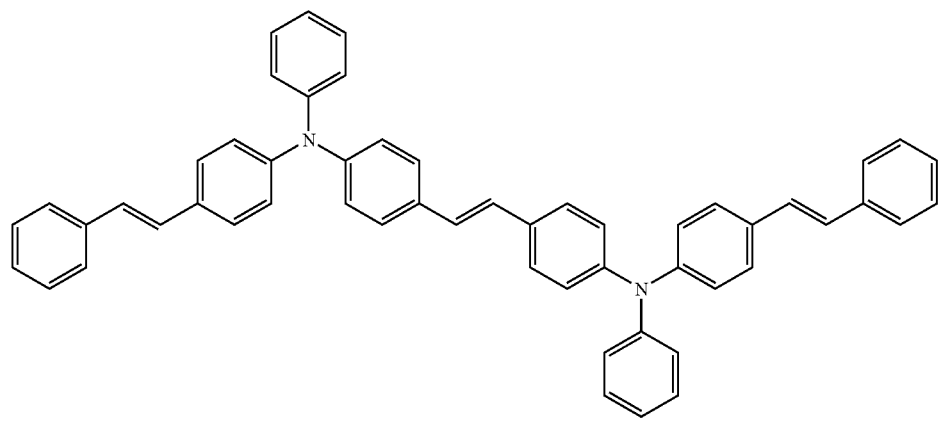

(D-2)

Examples 28 to 38

A light emitting device was produced in the same manner as Example 27 except for using materials described in Table 2 as host materials and dopant materials. The results of each example were shown in Table 2. D-3, D-4, D-5 and D-6 in Table 2 were compounds represented by the following formulae.

(D-3)

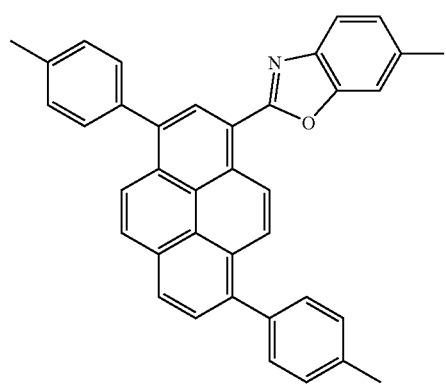

-continued (D-5)

(D-6)

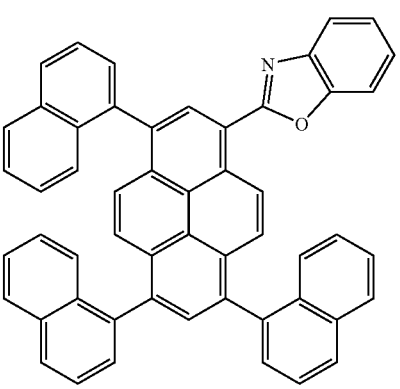

(D-4)

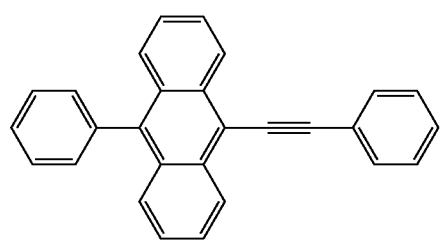

Example 39

A light emitting device was produced in the same manner as Example 9 except for using E-2 represented by the following formula as an electron transporting material. When this light emitting device was subject to a direct current drive of 10 mA/cm$^2$, blue light emission with a high luminous efficiency of 2.5 l m/W was obtained. When this light emitting device was subject to a direct drive current of 10 mA/cm$^2$, brightness half-life period was 2100 hours.

[Chemical formula 27]

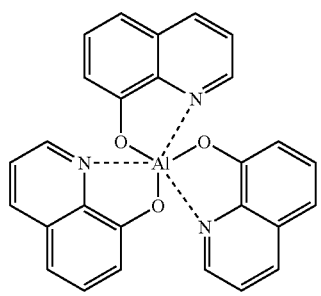
(E-2)

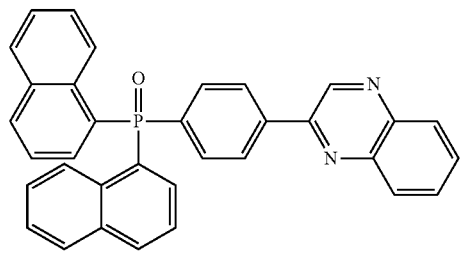
(E-4)

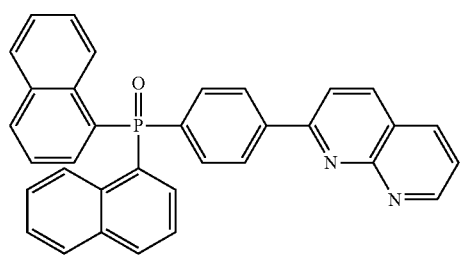
(E-5)

Examples 40 to 48

A light emitting device was produced in the same manner as Example 9 except for using materials described in Table 2 as host materials and electron transporting materials. The results of each example were shown in Table 2. E-3, E-4, E-5 and E-6 in Table 3 were compounds represented by the following formulae.

[Chemical formula 28]

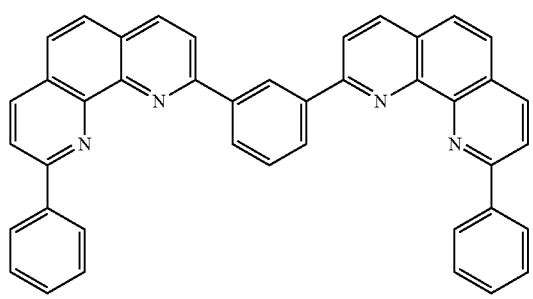
(E-3)

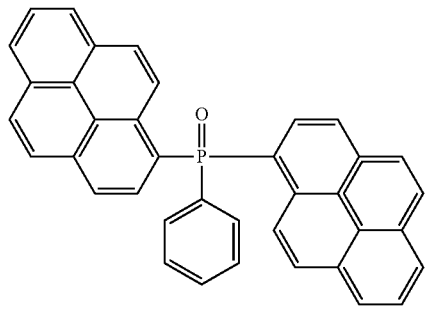
(E-6)

TABLE 2

|  | Light Emission Layer | | Electron Transporting Layer | Color of Light Emission | Luminous Efficiency (lm/W) | Brightness half-life period (h) |
| --- | --- | --- | --- | --- | --- | --- |
|  | Host Material | Dopant Material | | | | |
| Example 27 | Compound[3] | D-2 | E-1 | Blue | 2.6 | 2800 |
| Example 28 | Compound[3] | D-3 | E-1 | Blue | 2.1 | 4500 |
| Example 29 | Compound[3] | D-4 | E-1 | Blue | 2.3 | 4000 |
| Example 30 | Compound[58] | D-2 | E-1 | Blue | 2.7 | 3800 |
| Example 31 | Compound[58] | D-3 | E-1 | Blue | 2.1 | 4500 |
| Example 32 | Compound[58] | D-4 | E-1 | Blue | 2.3 | 4000 |
| Example 33 | Compound[103] | D-5 | E-1 | Blue | 2.5 | 7000 |
| Example 34 | Compound[132] | D-5 | E-1 | Blue | 2.6 | 6800 |
| Example 35 | Compound[56] | D-5 | E-1 | Blue | 2.6 | 7500 |
| Example 36 | Compound[57] | D-5 | E-1 | Blue | 2.5 | 7200 |
| Example 37 | Compound[135] | D-5 | E-1 | Blue | 2.8 | 8000 |
| Example 38 | Compound[103] | D-6 | E-1 | Blue | 3 | 7400 |
| Example 39 | Compound[3] | D-1 | E-2 | Blue | 2.5 | 2100 |
| Example 40 | Compound[3] | D-1 | E-3 | Blue | 4.1 | 3500 |
| Example 41 | Compound[3] | D-1 | E-4 | Blue | 3.8 | 2800 |
| Example 42 | Compound[3] | D-1 | E-5 | Blue | 3.6 | 2700 |
| Example 43 | Compound[3] | D-1 | E-6 | Blue | 3.5 | 2900 |
| Example 44 | Compound[58] | D-1 | E-2 | Blue | 2.5 | 5100 |
| Example 45 | Compound[58] | D-1 | E-3 | Blue | 4.1 | 5700 |
| Example 46 | Compound[58] | D-1 | E-4 | Blue | 3.7 | 3800 |

TABLE 2-continued

| | Light Emission Layer | | Electron Transporting Layer | Color of Light Emission | Luminous Efficiency (lm/W) | Brightness half-life period (h) |
|---|---|---|---|---|---|---|
| | Host Material | Dopant Material | | | | |
| Example 47 | Compound[58] | D-1 | E-5 | Blue | 3.6 | 3700 |
| Example 48 | Compound[58] | D-1 | E-6 | Blue | 3.4 | 3200 |

Example 49

A light emitting device was produced in the same manner as Example 9 except for not using a dopant material. When this light emitting device was subject to a direct current drive of 10 mA/cm$^2$, blue light emission with a luminous efficiency of 1.1 l m/W was obtained. When this light emitting device was subject to continuous drive with a direct current of 10 mA/cm$^2$, brightness half-life period was 2500 hours.

Example 50

A light emitting device was produced in the same manner as Example 49 except for using the compound [58] as a host material. When this light emitting device was subject to a direct current drive of 10 mA/cm$^2$, blue light emission with a luminous efficiency of 1.1 l m/W was obtained. When this light emitting device was subject to continuous drive with a direct current of 10 mA/cm$^2$, brightness half-life period was 5500 hours.

Example 51

A light emitting device was produced in the same manner as Example 9 except for using D-7 represented below as a dopant material so that doping concentration became 2%. When this light emitting device was subject to a direct current drive of 10 mA/cm$^2$, green light emission with a high luminous efficiency of 6.2 l m/W was obtained. When this light emitting device was subject to continuous drive with a direct current of 10 mA/cm$^2$, brightness half-life period was 2700 hours.

Example 52

A light emitting device was produced in the same manner as Example 51 except for using the compound [58] as a host material. When this light emitting device was subject to a direct current drive of 10 mA/cm$^2$, green light emission with a high luminous efficiency of 6.2 l m/W was obtained. When this light emitting device was subject to continuous drive with a direct current of 10 mA/cm$^2$, brightness half-life period was 3700 hours.

Example 53

A light emitting device was produced in the same manner as Example 9 except that, with regard to a luminescent material, the compound [3] was deposited as a host material and D-1 was deposited as a dopant material with a thickness of 5 nm so that doping concentration became 5%, and thereafter, with regard to another luminescent material, the compound [3] was laminated as a host material and D-8 represented below was laminated as a dopant material with a thickness of 30 nm so that doping concentration became 1%. When this light emitting device was subject to a direct current drive of 10 mA/cm$^2$, white light emission with a high luminous efficiency of 6.0 l m/W was obtained. When this light emitting device was subject to continuous drive with a direct current of 10 mA/cm$^2$, brightness half-life period was 4000 hours.

Example 54

A light emitting device was produced in the same manner as Example 53 except for using the compound [58] as a host material. When this light emitting device was subject to a direct current drive of 10 mA/cm$^2$, white light emission with a high luminous efficiency of 6.0 l m/W was obtained. When this light emitting device was subject to continuous drive with a direct current of 10 mA/cm$^2$, brightness half-life period was 4500 hours.

Example 55

A glass substrate (manufactured by ASAHI GLASS CO., LTD., 15 Ω/square, electron beam deposition product) on which an ITO transparent conductive film was accumulated with a thickness of 150 nm was cut to a size of 30×40 mm, which ITO conductive film was patterned into a stripe of 300 μm-pitch (a residual width of 270 μm)×32 pieces by a photolithographic method. One side of the ITO stripe in a long side direction was widened to 1.27 mm-pitch (an opening width of 800 μm) in order to facilitate electrical connection to the exterior. The obtained substrate was subject to ultrasonic cleaning with each of acetone and "SEMICOCLEAN (registered trademark) 56" (manufactured by Furuchi Chemical Corporation) for 15 minutes, and then cleaned with ultrapure water. Subsequently, the substrate was subject to ultrasonic cleaning with isopropyl alcohol for 15 minutes, and then immersed in hot methanol for 15 minutes and dried. Immediately before producing a device, this substrate was subject to UV-ozone treatment for 1 hour and further placed in a vacuum evaporator to exhaust until degree of vacuum in the evaporator became 5×10$^{-4}$ Pa or less. First, through a resistance heating method, 4,4'-bis(N-(meta-tolyl)-N-phenylamino)biphenyl was deposited with a thickness of 150 nm as a hole transporting material. Next, the compound [67] was deposited as a host material and D-1 was deposited as a dopant material with a thickness of 35 nm so that doping concentration became 5%. Next, E-1 was laminated with a thickness of 20 nm as an electron transporting material. The film thickness herein was an indicated value of a crystal oscillation film thickness monitor. Next, a mask such that 16 pieces of 250 μm-opening (corresponding to a residual width of 50 μm and 300 μm-pitch) were made on a Kovar plate with a thickness of 50 μm by wet etching was subject to mask exchange so as to be orthogonal to the ITO stripe in a vacuum and fixed by a magnet from the back surface so that the mask and the ITO substrate adhered closely. The organic layer was doped with lithium to a thickness of 0.5 nm to thereafter deposit aluminum with a thickness of 200 nm and produce a 32×16-dot matrix device. When the device was subject to matrix drive, characters were indicated without crosstalk.

INDUSTRIAL APPLICABILITY

A light emitting device of the present invention is appropriately utilizable in the fields such as display device, flat-panel display, backlight, illumination, interior, mark, signboard, electrophotographic apparatus and light signal generator.

What is claimed is:

1. A light emitting device material comprising an anthracene compound represented by general formula (1):

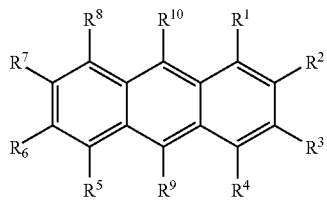

(1)

wherein $R^1$ to $R^8$ and $R^{10}$ each may be the same or different and are selected from among a hydrogen atom, alkyl group, cycloalkyl group, heterocyclic group, alkenyl group, cycloalkenyl group, alkynyl group, alkoxy group, alkylthio group, arylether group, arylthioether group, aryl group, heteroaryl group, halogen atom, cyano group, carbonyl group, carboxyl group, oxycarbonyl group, carbamoyl group, amino group, silyl group and phosphine oxide group, and at least $R^9$ is a substituent represented by the following general formula (2):

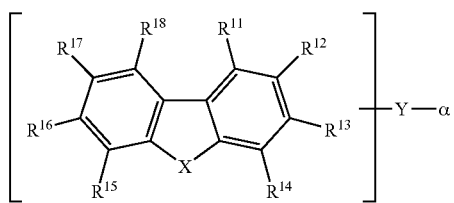

(2)

wherein $R^{11}$ to $R^{18}$ each may be the same or different and are selected from among a hydrogen atom, alkyl group, cycloalkyl group, alkoxy group, phenyl group, naphtyl group and heteroaryl group, X represents an oxygen atom or sulfur atom, and Y is selected from among arylene group and heteroarylene group, and any one of the $R^{11}$ to $R^{18}$ is used for linking with Y, and optionally α is used for linking with the anthracene compound of formula (1).

2. A light emitting device material according to claim 1, comprising an anthracene compound represented by the general formula (1), and in that X of the general formula (2) is an oxygen atom.

3. A light emitting device comprising at least a luminescent layer between an anode and a cathode, the luminescent layer comprising the light emitting device material of claim 1.

4. A light emitting device according to claim 3, wherein the luminescent layer comprises a host material and a dopant material, and wherein the host material comprises the light emitting device material containing an anthracene compound represented by the general formula (1).

5. A light emitting device according to claim 3, comprising at least an electron transporting layer between the luminescent layer and the cathode, wherein the electron transporting layer contains a compound having a heteroaryl ring structure containing electron accepting nitrogen, and wherein the compound comprises an element selected from among carbon, hydrogen, nitrogen, oxygen, silicon and phosphorus.

* * * * *